United States Patent
Hamase et al.

(10) Patent No.: US 10,393,749 B2
(45) Date of Patent: Aug. 27, 2019

(54) MARKER FOR EARLY DIAGNOSIS OF KIDNEY FAILURE

(71) Applicant: Shiseido Company, Ltd., Chuo-ku, Tokyo (JP)

(72) Inventors: Kenji Hamase, Fukuoka (JP); Yurika Miyoshi, Fukuoka (JP); Masashi Mita, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 285 days.

(21) Appl. No.: 15/103,539

(22) PCT Filed: Dec. 11, 2014

(86) PCT No.: PCT/JP2014/082899
§ 371 (c)(1),
(2) Date: Jun. 10, 2016

(87) PCT Pub. No.: WO2015/087985
PCT Pub. Date: Jun. 18, 2015

(65) Prior Publication Data
US 2016/0313342 A1    Oct. 27, 2016

(30) Foreign Application Priority Data
Dec. 11, 2013  (JP) ................................ 2013-256224

(51) Int. Cl.
*G01N 33/68*    (2006.01)
(52) U.S. Cl.
CPC ... *G01N 33/6812* (2013.01); *G01N 2800/347* (2013.01)
(58) Field of Classification Search
CPC ............................................... G01N 33/6812
See application file for complete search history.

(56) References Cited

U.S. PATENT DOCUMENTS

2006/0046268 A1*  3/2006  Devore ............ G01N 33/56972
                                                     435/7.1
2009/0075284 A1   3/2009  Chinnaiyan et al.
                          (Continued)

FOREIGN PATENT DOCUMENTS

EP            2249161 A1    11/2010
WO    WO 00/70329 A1       11/2000
                          (Continued)

OTHER PUBLICATIONS

Ischemic Acute Kidney Injury Perturbs Homeostasis of Serine Enantiomers in the body luid in Mice: Early Detection of Renal Dysfunction Using the Ratio of Serine Enantiomers Sasabe et al. PLoS One Jan. 2014, vol. 9, Issue 1, pp. 1-9 (Year: 2014).*
(Continued)

*Primary Examiner* — Lyle Alexander
*Assistant Examiner* — Dwan A Gerido
(74) *Attorney, Agent, or Firm* — Foley & Lardner LLP

(57) ABSTRACT

The present invention addresses the problem of identifying a biomarker of renal failure, said biomarker being available from urine or blood, and fluctuating from an early stage than glomerular filtration rate and serum creatinine level, and thus developing a technique for diagnosing early stage kidney failure. A method for analyzing the blood, plasma, serum or urine of a renal failure suspected subject comprises a step of measuring the concentration of a pair of D-form and L-form of at least one amino acid selected from the amino acid group consisting of [D-serine] and [L-serine], etc., contained in the blood, plasma, serum or urine of the subject, and calculating, as an pathological index of the subject, the ratio of the D-form concentration to the L-form concentration or the percentage of the D-form concentration relative to the total concentration of the D-form and L-form.

17 Claims, 19 Drawing Sheets

(56) References Cited

U.S. PATENT DOCUMENTS

| | | | |
|---|---|---|---|
| 2009/0148533 A1* | 6/2009 | Charmot | A61K 9/1635 424/497 |
| 2015/0079623 A1* | 3/2015 | Hamase | G01N 33/6806 435/29 |

FOREIGN PATENT DOCUMENTS

| | | |
|---|---|---|
| WO | WO 2004/081527 A2 | 9/2004 |
| WO | WO 2013/140785 A1 | 9/2013 |

OTHER PUBLICATIONS

Brueckner et al., "Gas chromatographic characterization of free D-amino acids in the blood serum of patients with renal disorders and of healthy volunteers," Journal of Chromatography, 1993, 614:7-17.

Corrigan, John J., "D-Amino Acids in Animals," Science, Apr. 11, 1969, 164:142-149.

D'Anellio et al., "Occurrence of D-aspartic acid and N-methyl-D-aspartic acid in rat neuroendocrine tissues and their role in the modulation of luteinizing hormone and growth hormone release," The FASEB Journal, Apr. 2000, 14:699-714.

Fukushima et al., "Determination of D-Amino Acids in Serum from Patients with Renal Dysfunction," Biol. Pharm. Bull., 1995, 18(8):1130-1132.

Hamase et al., "Simultaneous determination of hydrophilic amino acid enantiomers in mammalian tissues and physiological fluids applying a fully automated micro-two-dimensional high-performance liquid chromatographic concept," Journal of Chromatography A, 2010, 1217:1056-1062.

Hamase et al., "Comprehensive analysis of branched aliphatic D-amino acids in mammals using an integrated multi-loop two-dimensional column-switching high-performance liquid chromatographic system combining reversed-phase and enantioselective columns," Journal of Chromatography A, 2007, 1143:105-111.

Hamase et al., "D-Amino acids in mammals and their diagnostic value," Journal of Chromatography B, 2002, 781:73-91.

Huang et al., "Urinary Excretion of D-Serine in Human: Comparison of Different Ages and Species," Biol. Pharm. Bull, 1998, 21(2):156-162.

Ishida, Hironori, "Serum D-Amino Acid Elucidated in Renal Failure," Department of Urology, Kitasato University School of Medicine, Kitasoto Med., 1993, 23:51-62, with English summary on p. 62.

KDIGO 2012 Clinical Practice Guideline for the Evaluation and Management of Chromic Kidney Disease, Supplements 1, 2013, 162 pages.

Miyoshi et al., "Simultaneous two-dimensional HPLC determination of free D-serine and D-alanine in the brain and periphery of mutant rats lacking D-amino-acid oxidase," Journal of Chromatography B, 2011, 879:3184-3189.

Nagata, Yoko, "Neutral free D-amino acids present in human plasma," Viva Origino, Jul. 1990, 18(2):88-89, with English translation.

Nagata et al., "D-Aspartate stimulation of testosterone synthesis in rat Leydig cells," FEBS Letters, 1999, 444:160-164.

Nishikawa, Toru, "Metabolism and Functional Roles of Endogeneous D-Serine in Mammalian Brains," Biol. Pharm. Bull, 2005, 28(9):1561-1565.

Sasabe et al., "Ischemic Acute Kidney Injury Perturbs Homeostasis of Serine Enantiomers in the Body Fluid in Mice: Early Detection of Renal Dysfunction Using the Ratio of Serine Enantiomers," PLoS One, Jan. 2014, 9(1):e86504:1-9.

Slocum et al., "Marking renal injury: can we move beyond serum creatinine?", Translational Research, Apr. 2012, 159:277-289.

Waldhier et al., "Improved enantiomer resolution and quantification of free D-amino acids in serum and urine by comprehensive two-dimensional gas chromatography-time-of-flight mass spectrometry," Journal of Chromatography A, 2011, 1218:4537-4544.

Waldhier et al., "Comparison of derivatization and chromatographic methods for GC-MS analysis of amino acid enantiomers in physiological samples," Journal of Chromatography B, 2010, 878:1103-1112.

Young et al., "D-Amino acids in chromic renal failure and the effects of dialysis and urinary losses," Amino Acids, 1994, 6:283-293.

Zhang et al., "Study on the decrease of renal D-amino acid oxidase activity in the rat after renal ischemia by chiral ligand exchange capillary electrophoresis," Amino Acids, 2012, 42:337-345.

* cited by examiner

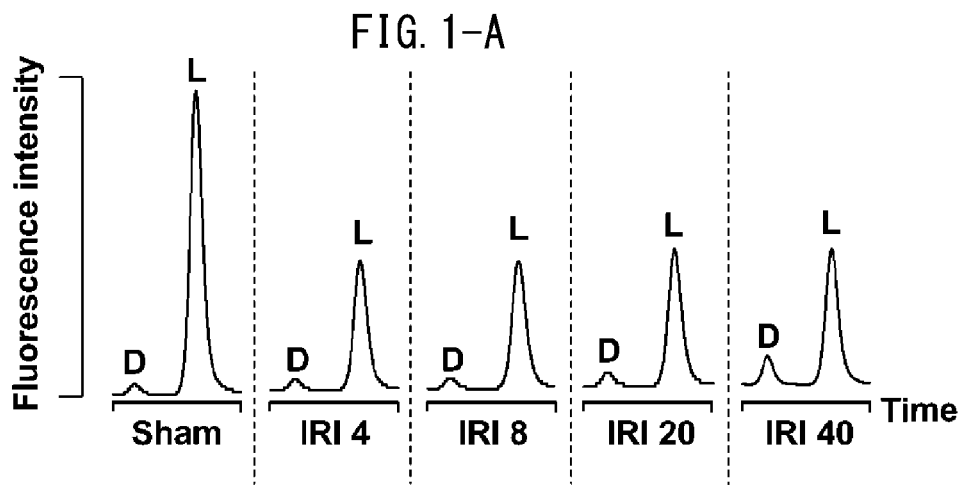
FIG. 1-A
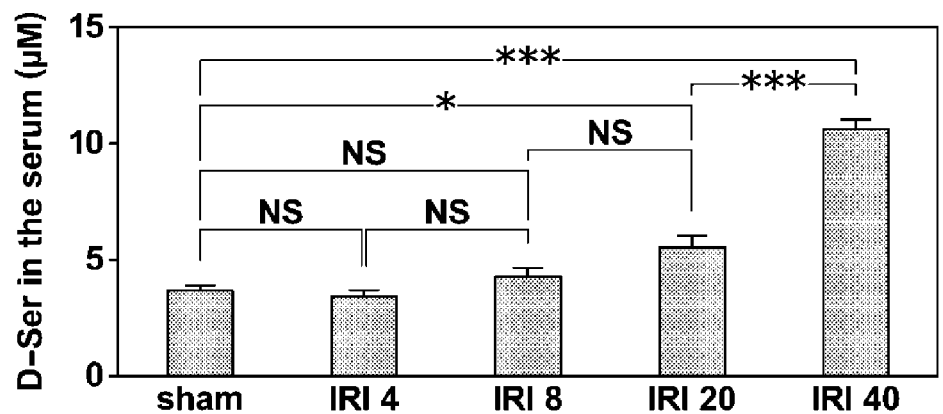
FIG. 1-B
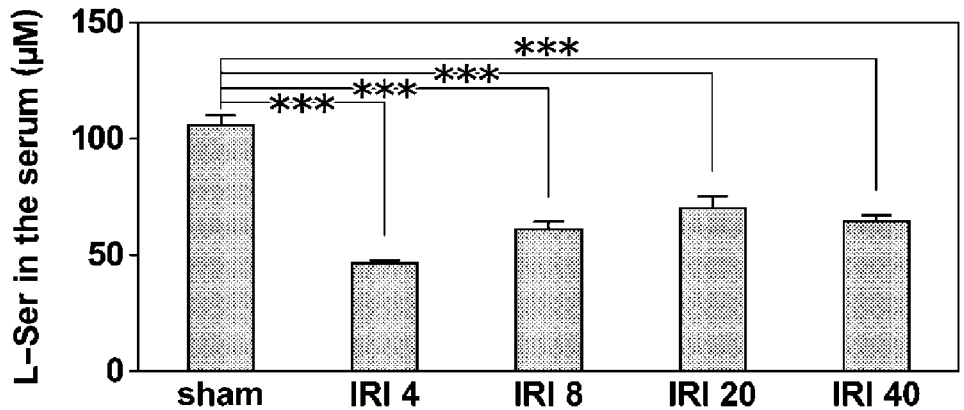
FIG. 1-C

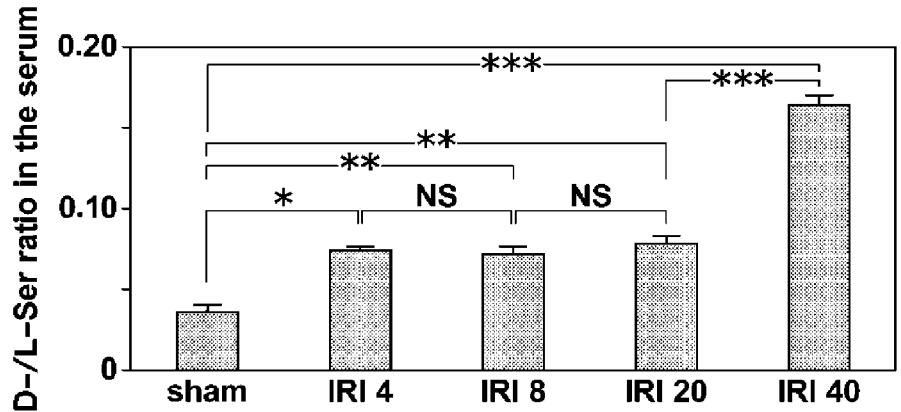
FIG. 1-D
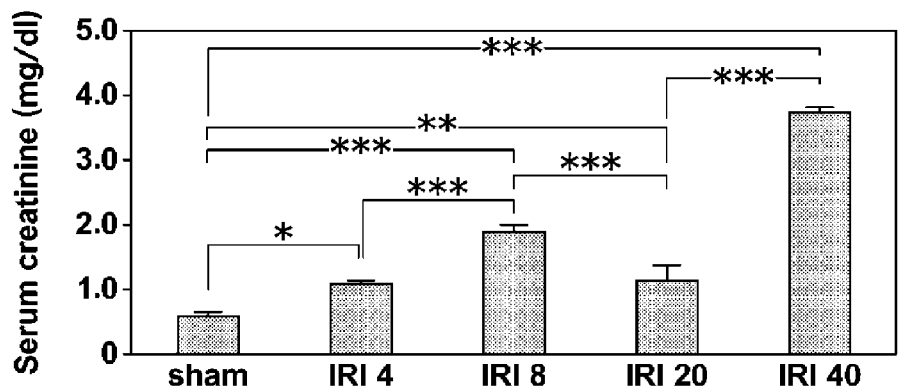
FIG. 1-E
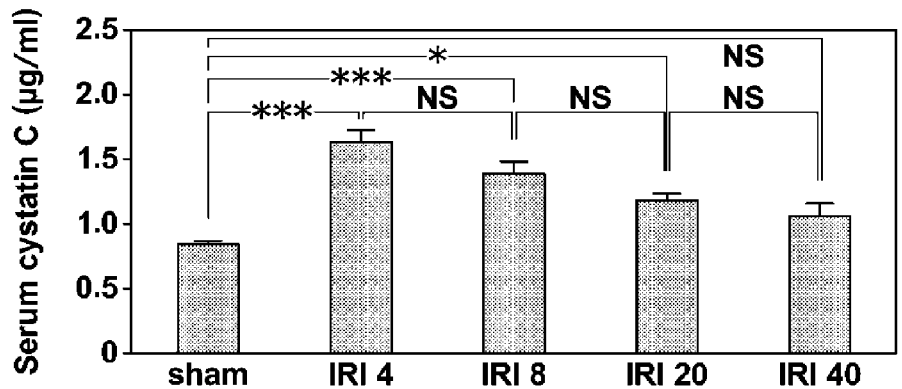
FIG. 1-F

FIG. 2-A
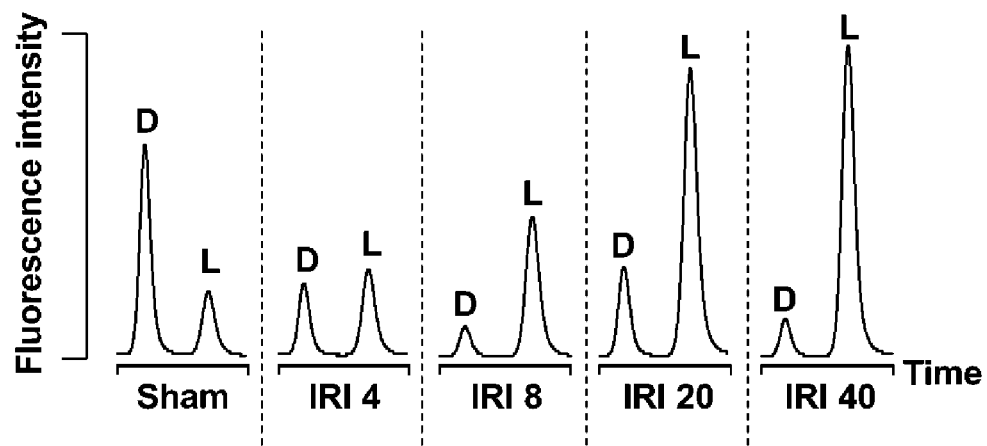
FIG. 2-B
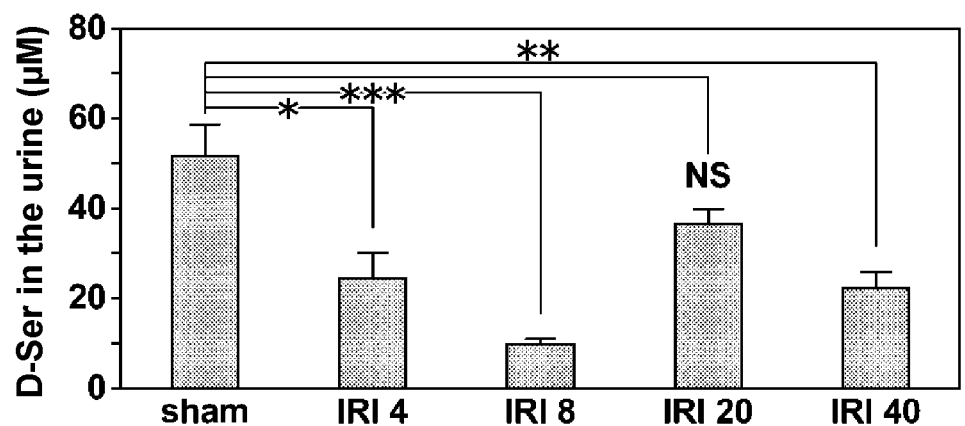
FIG. 2-C
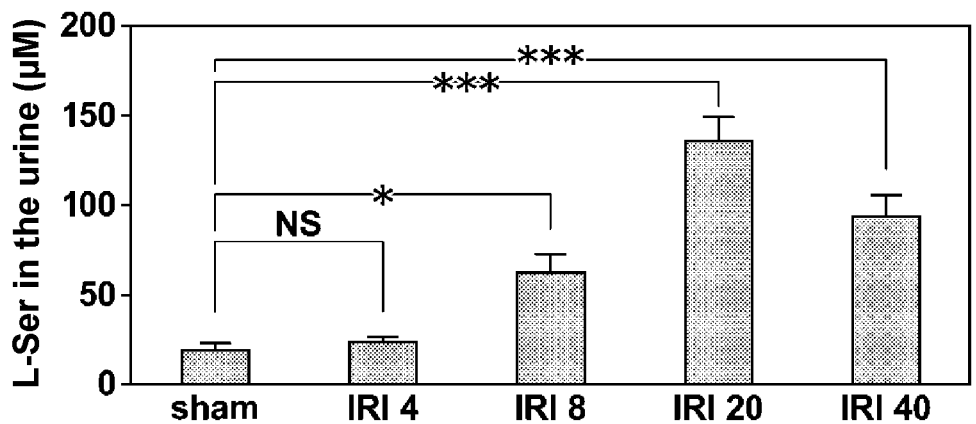

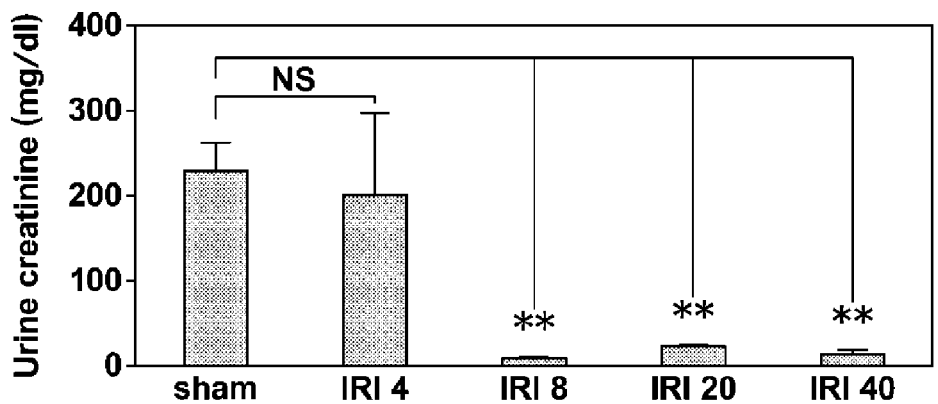
FIG. 2-D
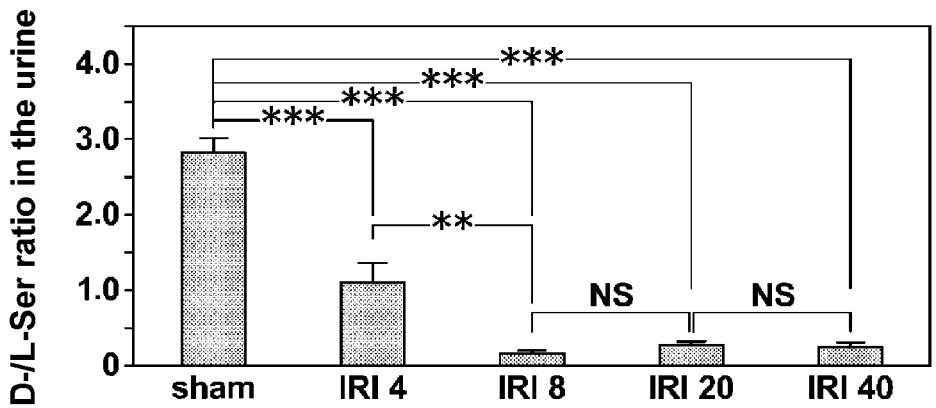
FIG. 2-E
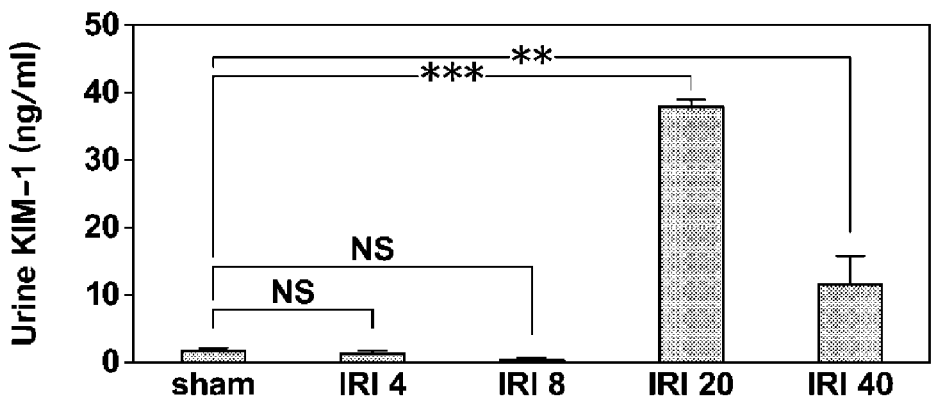
FIG. 2-F

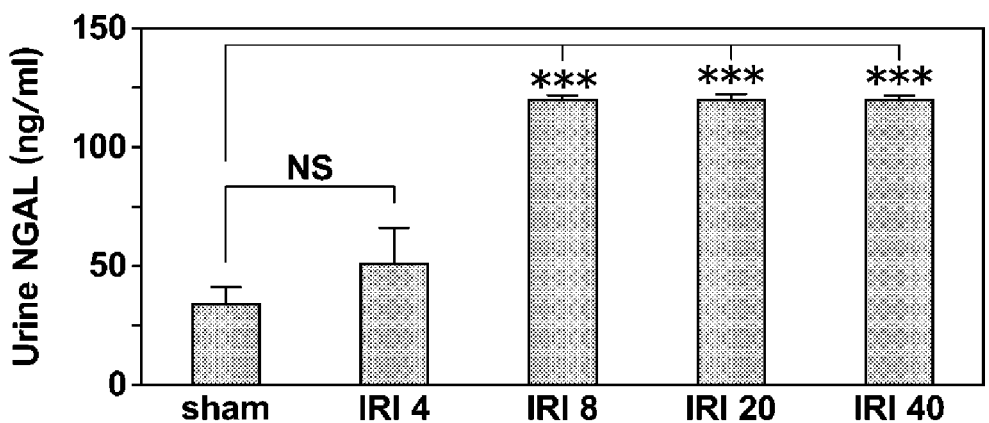
FIG. 2-G
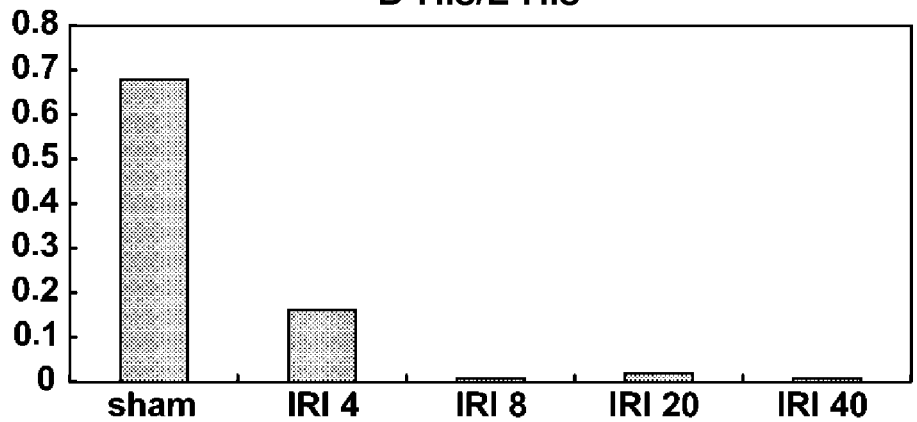
FIG. 3-A
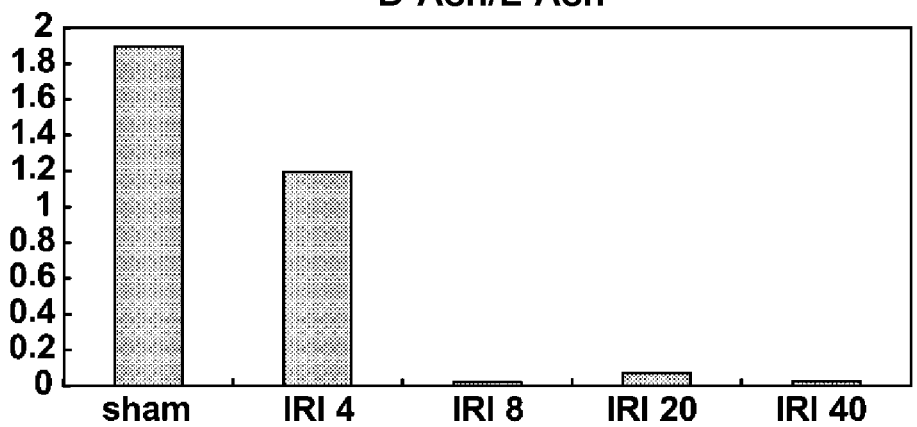
FIG. 3-B

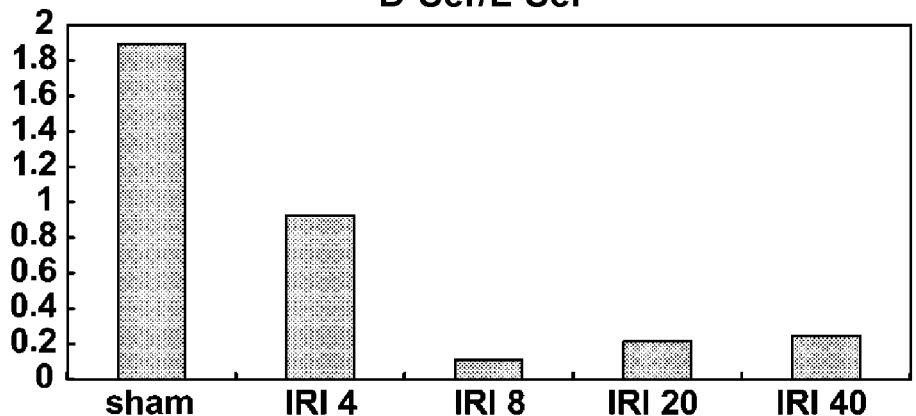
FIG. 3-C
D-Ser/L-Ser
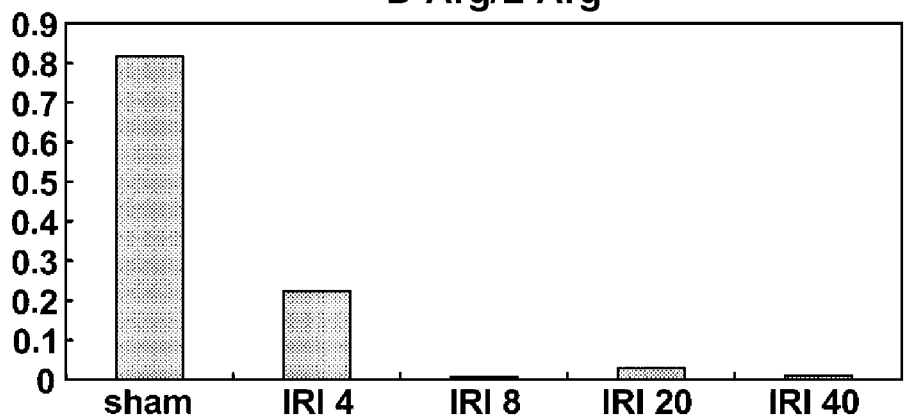
FIG. 3-D
D-Arg/L-Arg
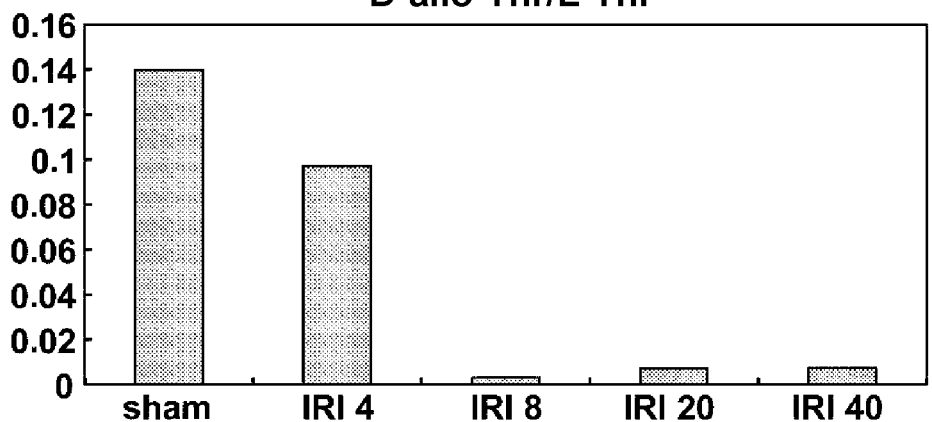
FIG. 3-E
D-allo-Thr/L-Thr

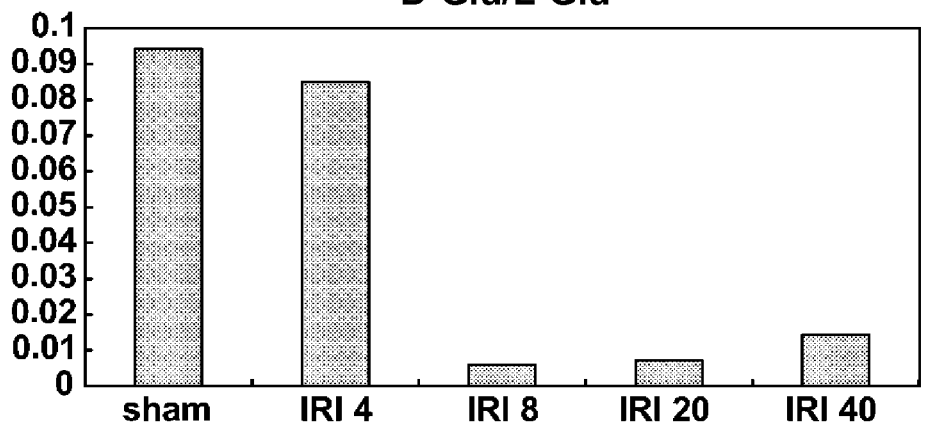
FIG. 3-F
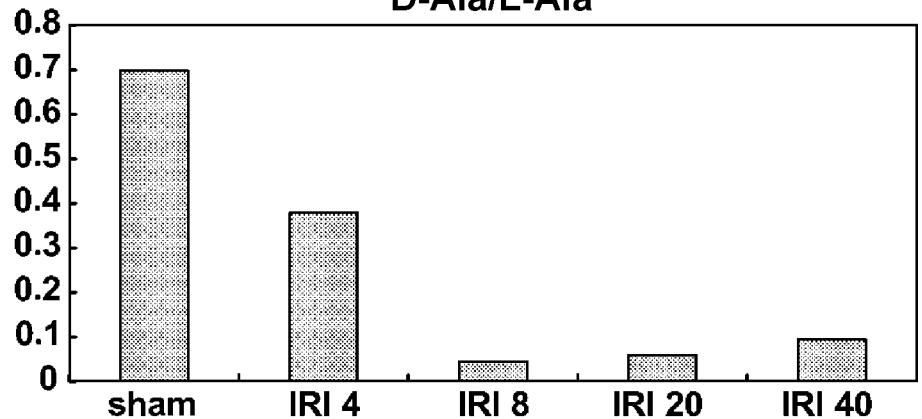
FIG. 3-G
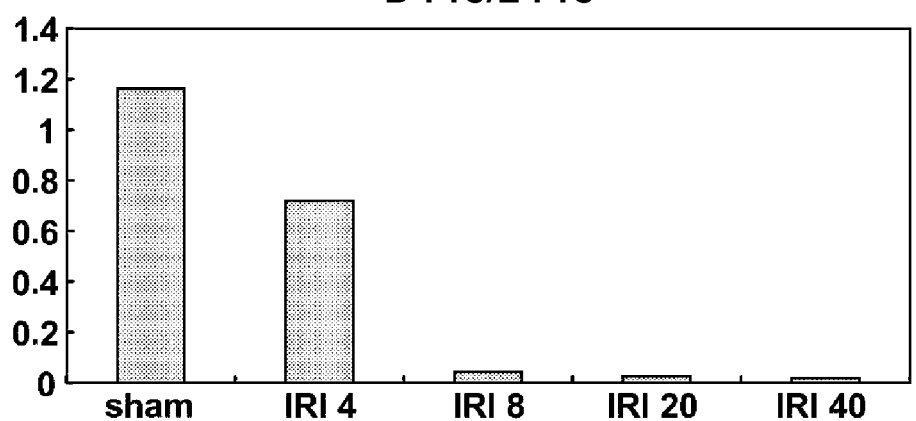
FIG. 3-H

FIG. 3-I
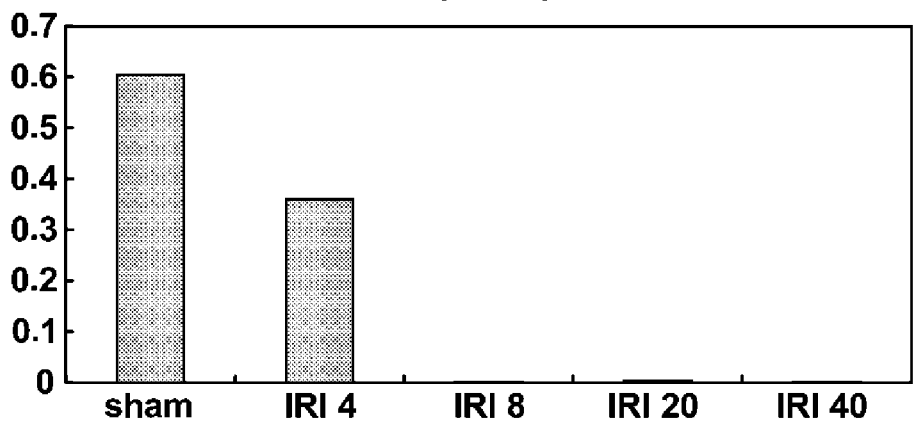
FIG. 3-J
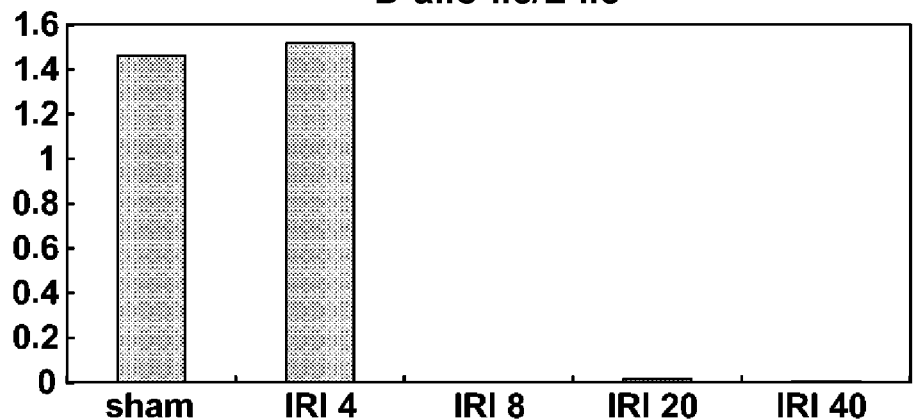
FIG. 3-K
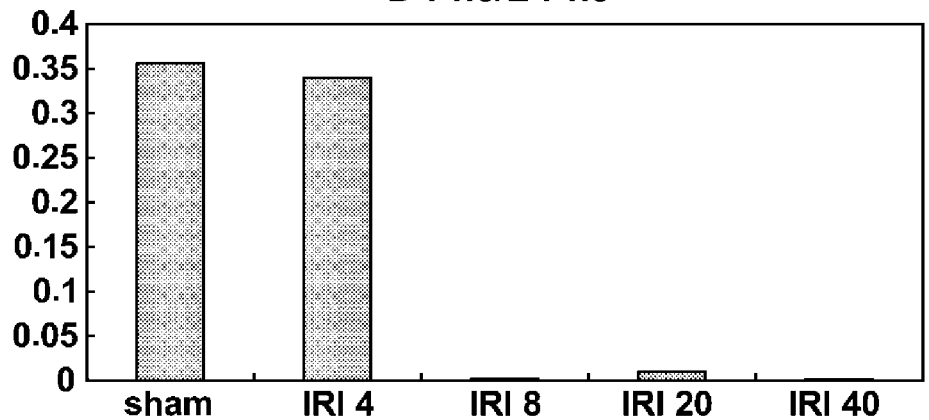

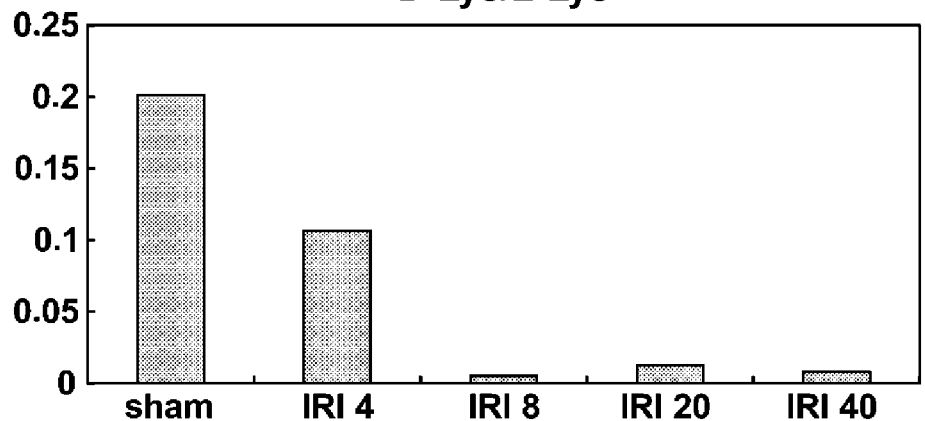
FIG. 3-L
D-Lys/L-Lys
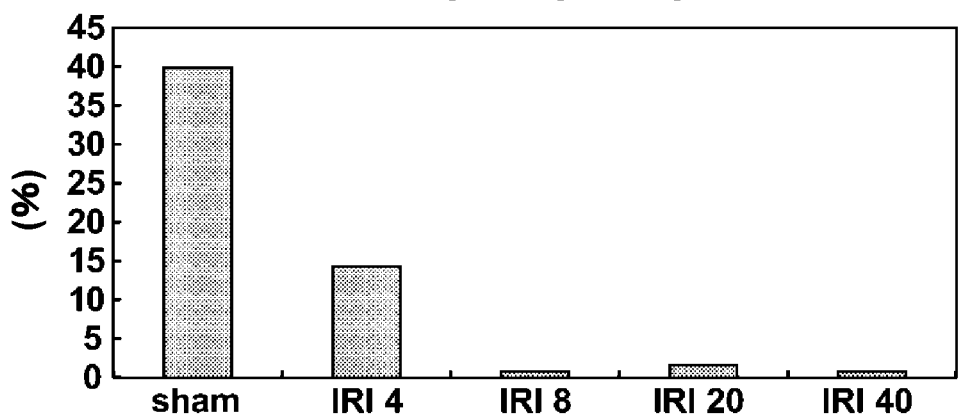
FIG. 4-A
D-His/D-His+L-His
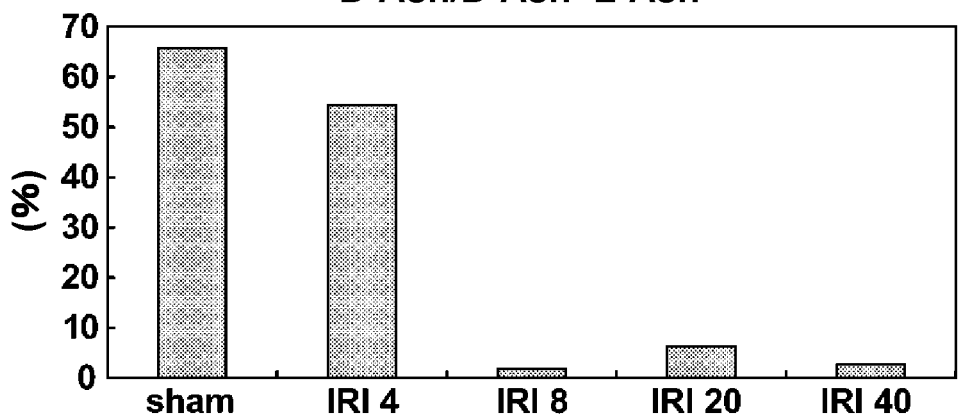
FIG. 4-B
D-Asn/D-Asn+L-Asn

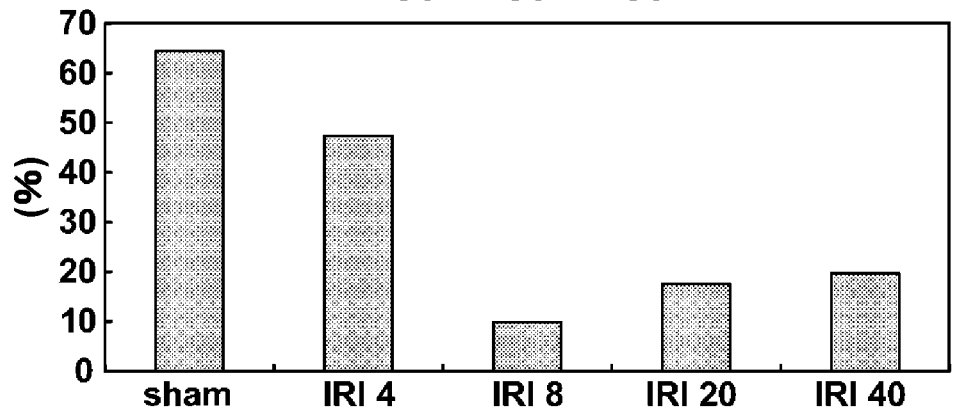
FIG. 4-C
D-Ser/D-Ser+L-Ser
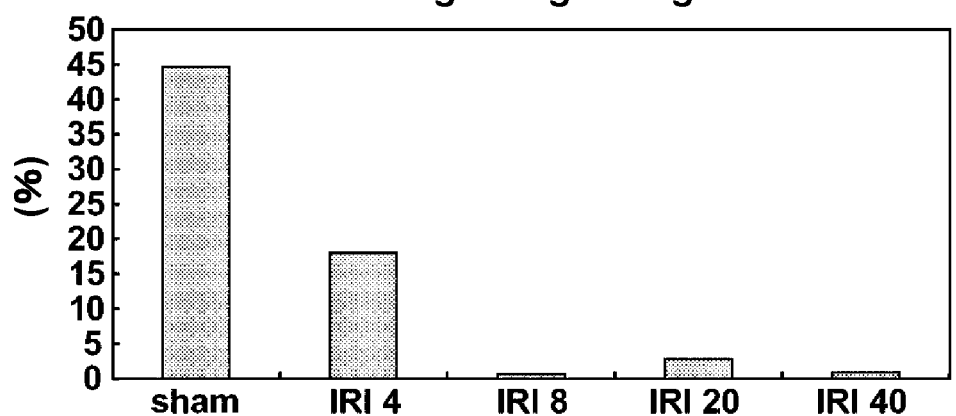
FIG. 4-D
D-Arg/D-Arg+L-Arg
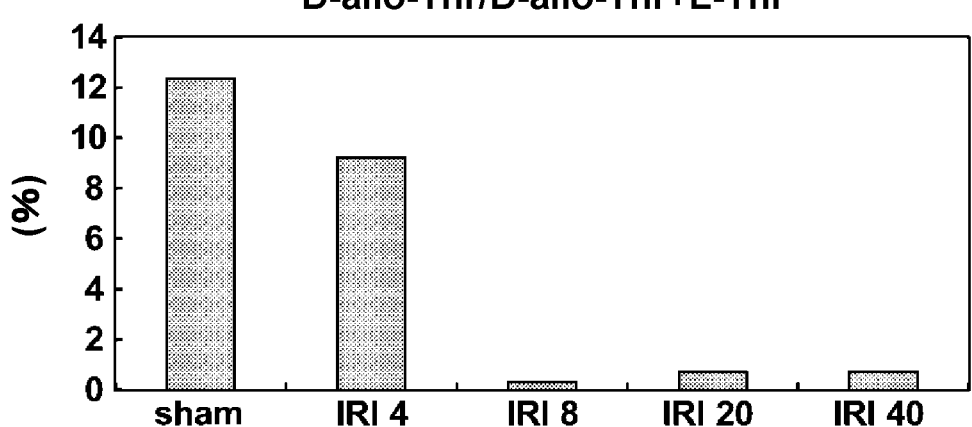
FIG. 4-E
D-allo-Thr/D-allo-Thr+L-Thr

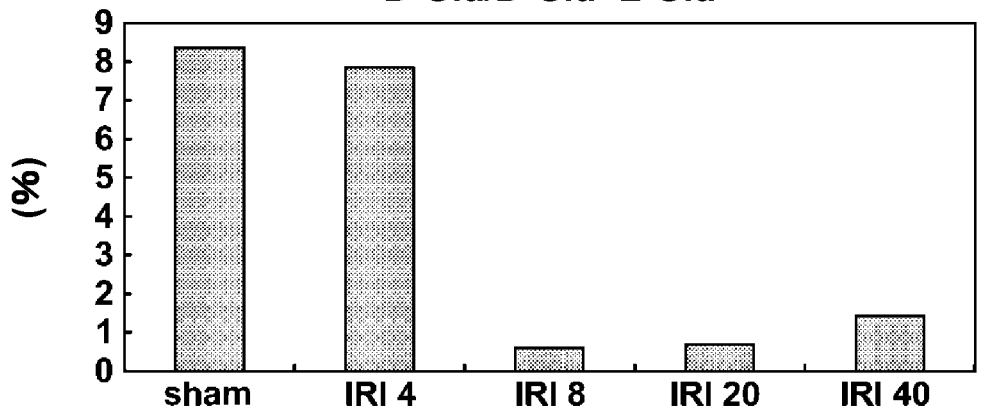
FIG. 4-F
D-Glu/D-Glu+L-Glu
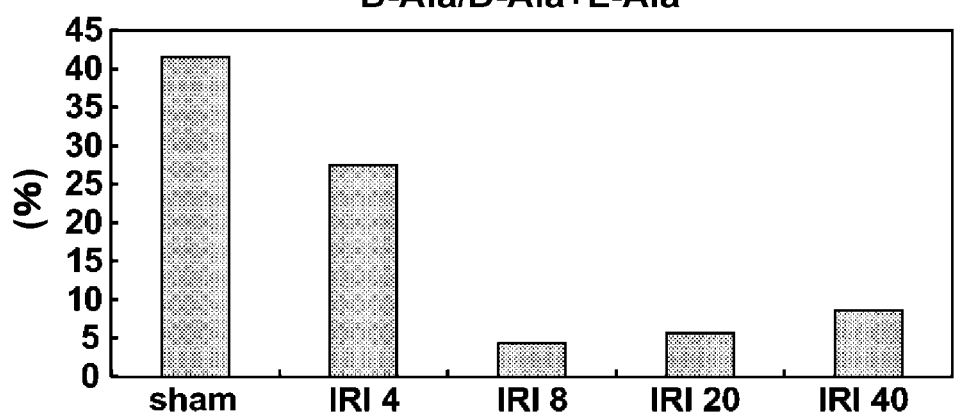
FIG. 4-G
D-Ala/D-Ala+L-Ala
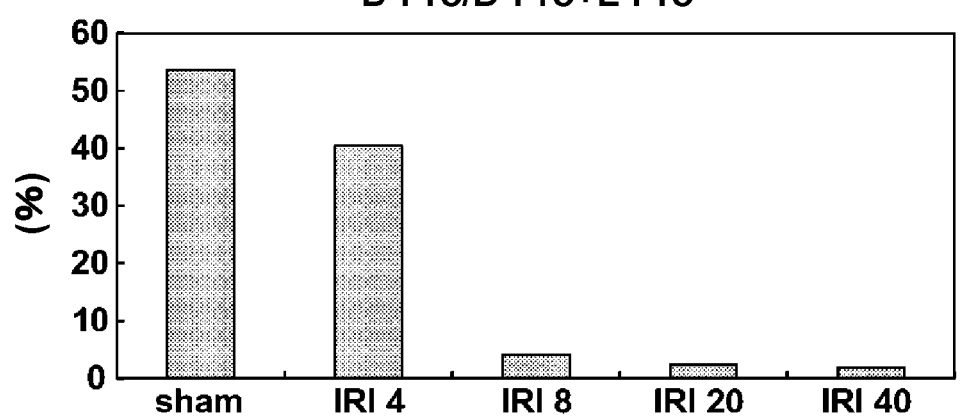
FIG. 4-H
D-Pro/D-Pro+L-Pro

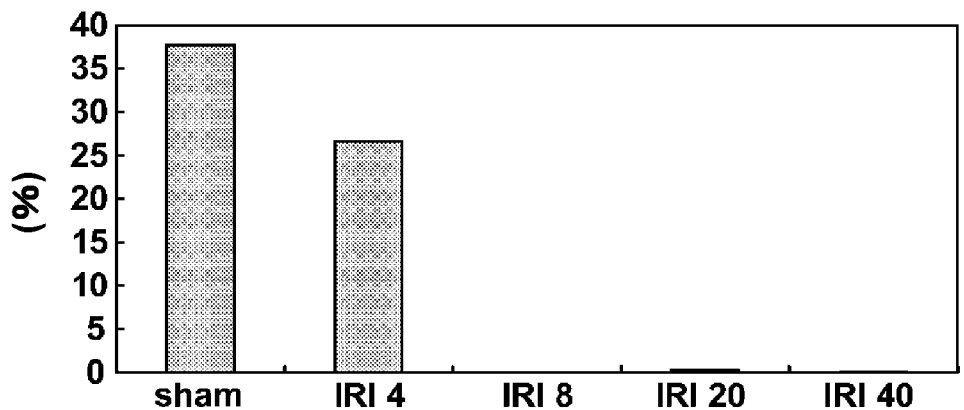
FIG. 4-I
D-Val/D-Val+L-Val
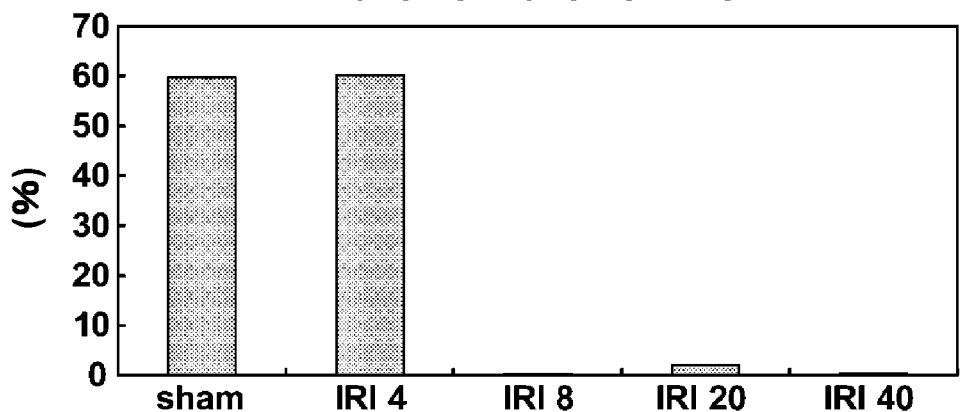
FIG. 4-J
D-allo-Ile/D-allo-Ile+L-Ile
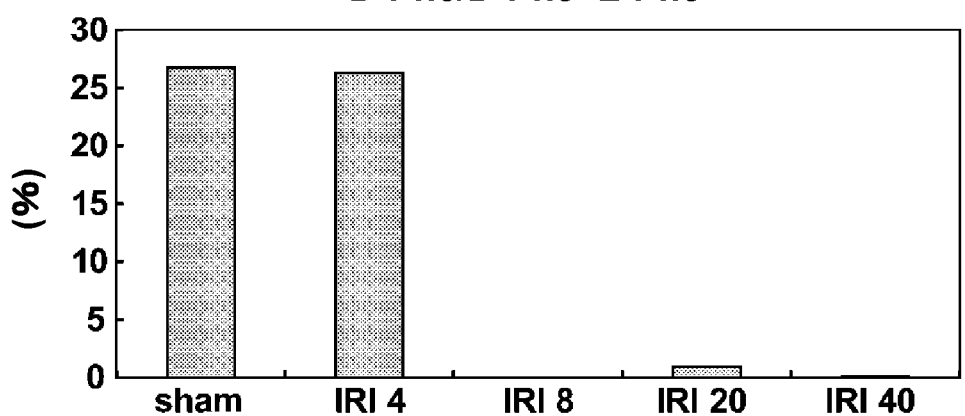
FIG. 4-K
D-Phe/D-Phe+L-Phe

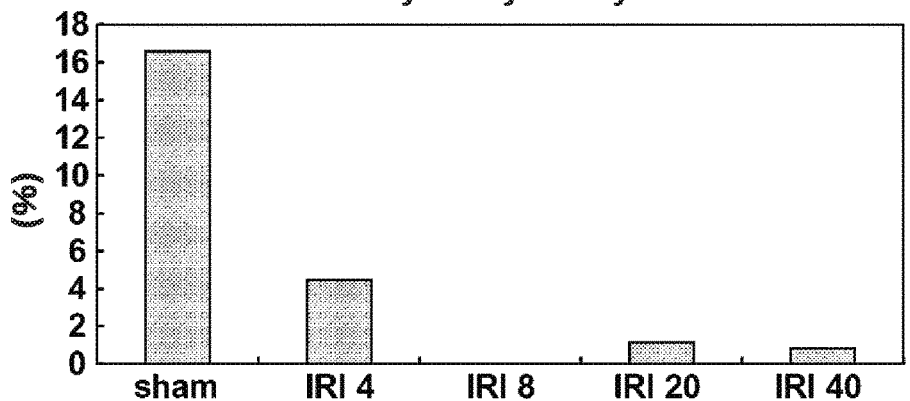
FIG. 4-L
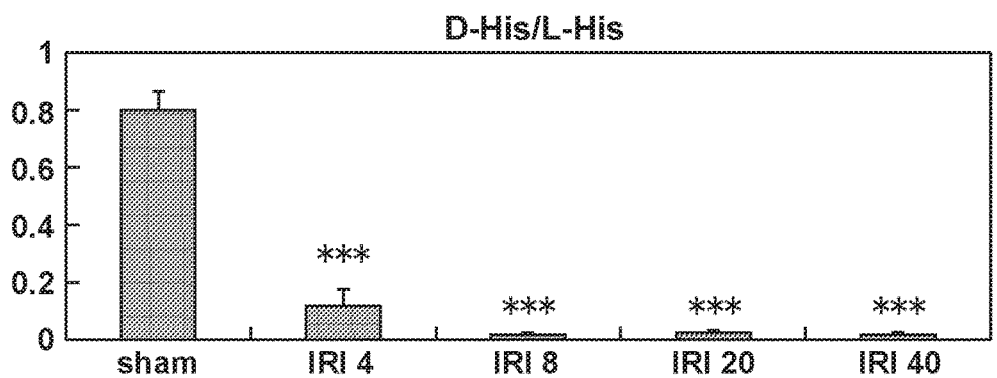
FIG. 5-A
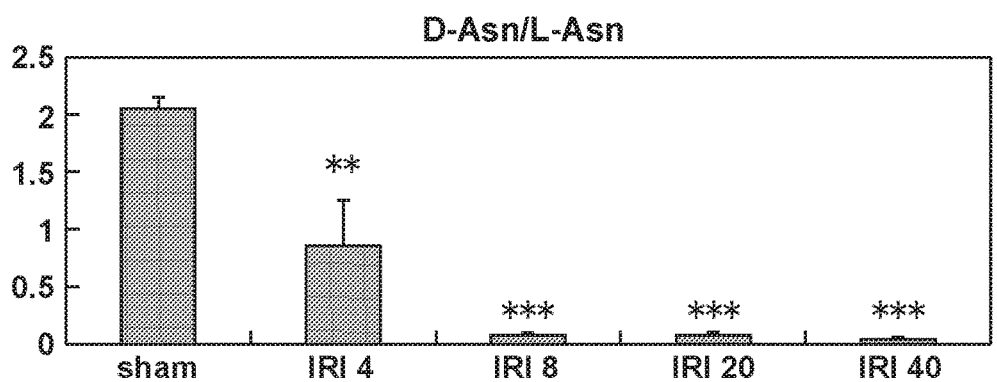
FIG. 5-B

FIG. 5-C
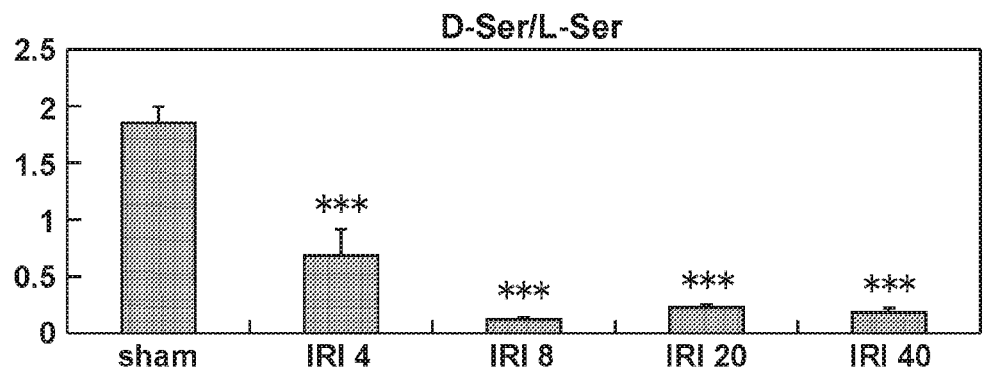
FIG. 5-D
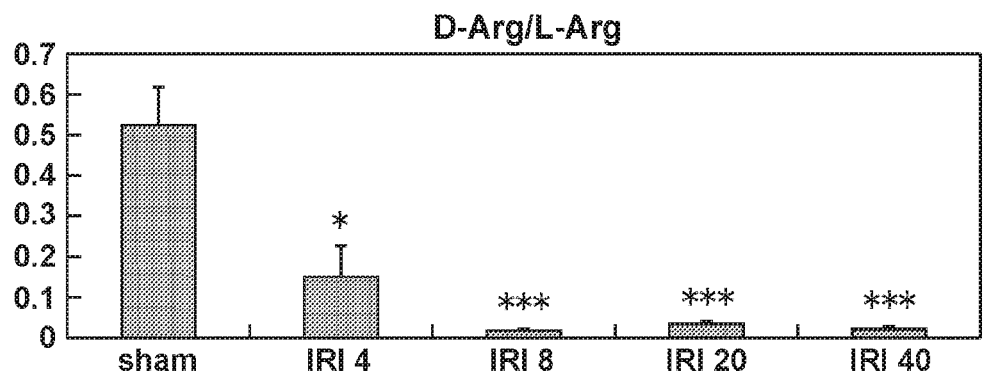
FIG. 5-E
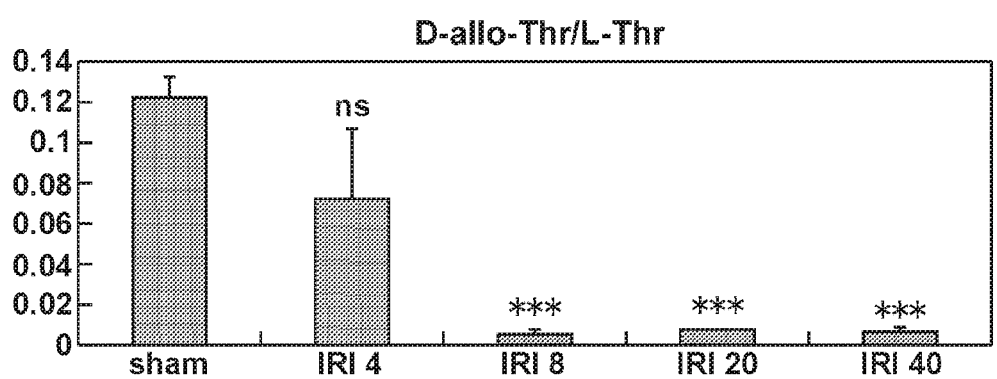

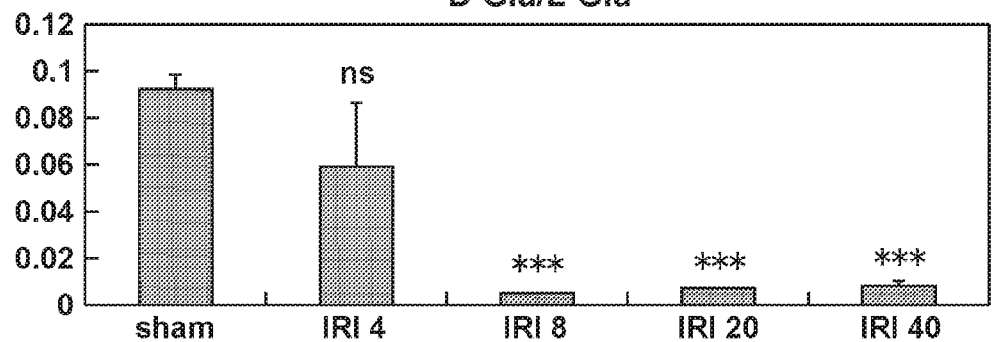
FIG. 5-F
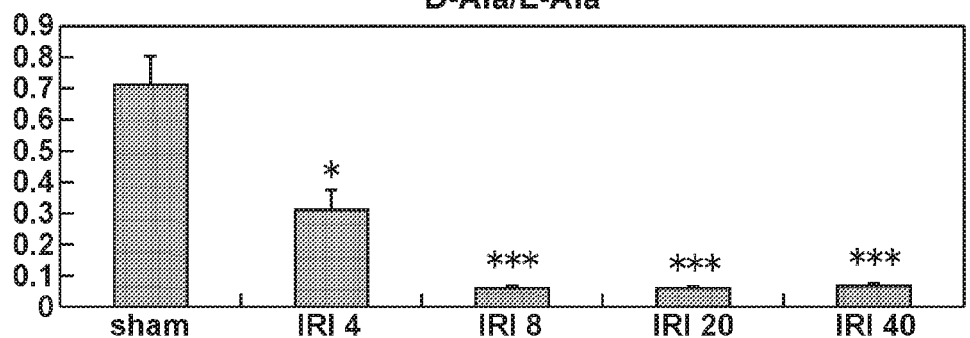
FIG. 5-G
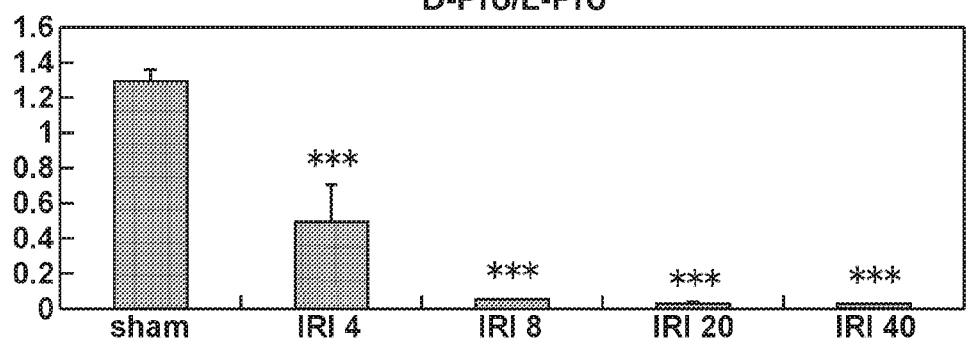
FIG. 5-H

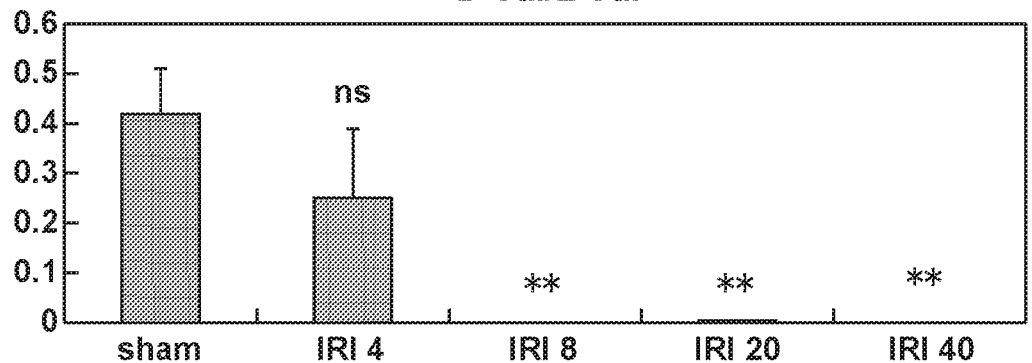
FIG. 5-I
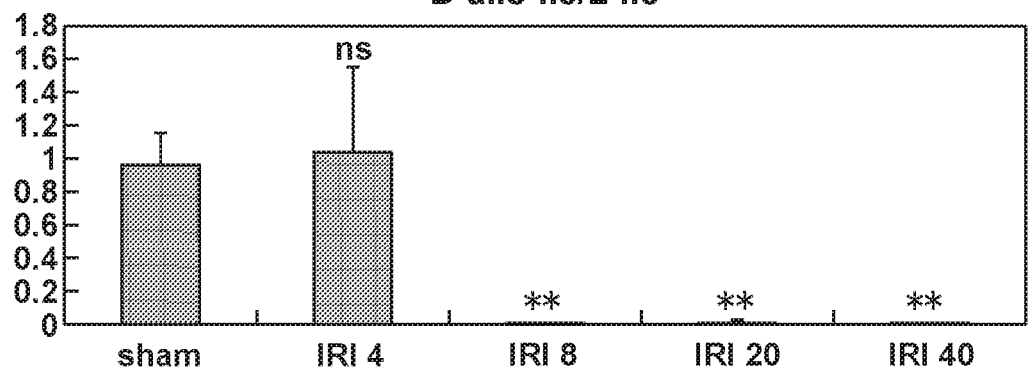
FIG. 5-J
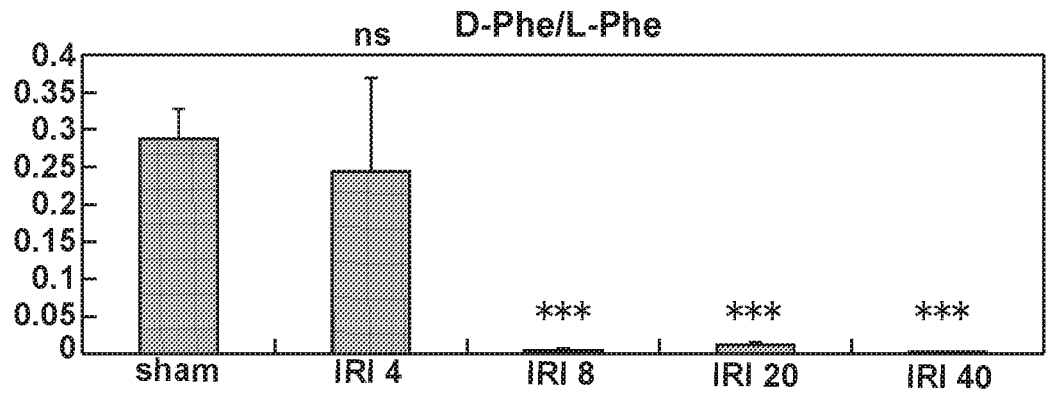
FIG. 5-K

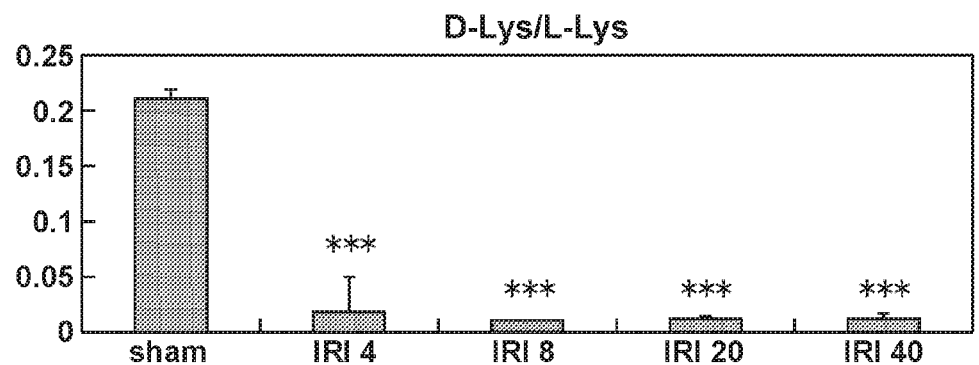
FIG. 5-L
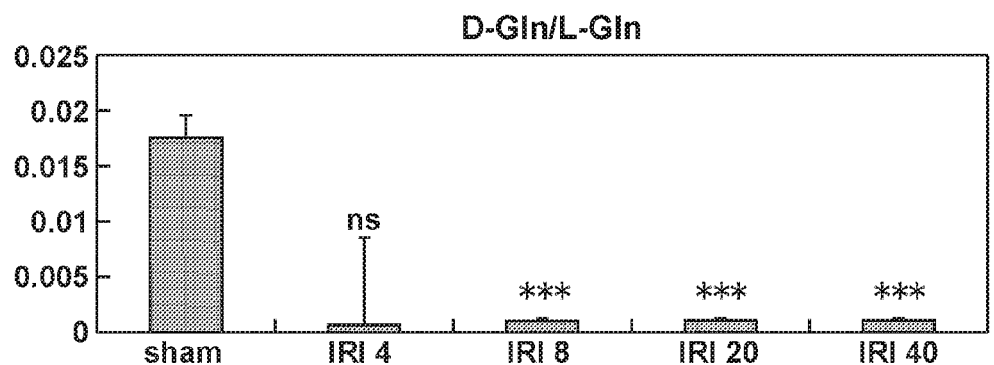
FIG. 5-M
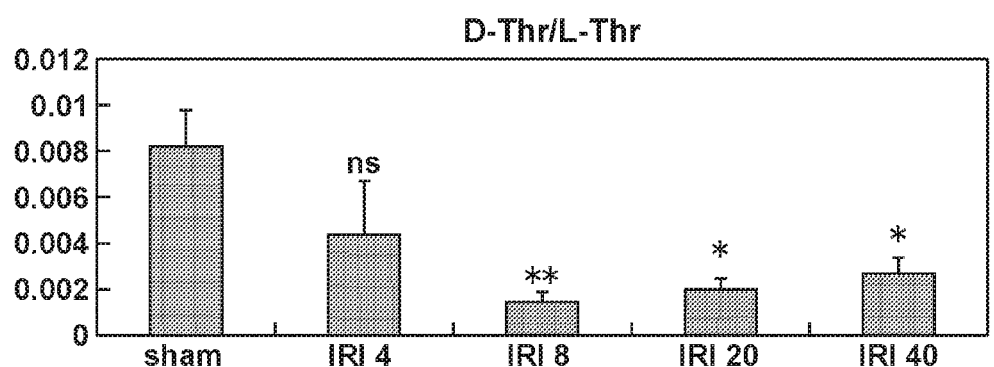
FIG. 5-N

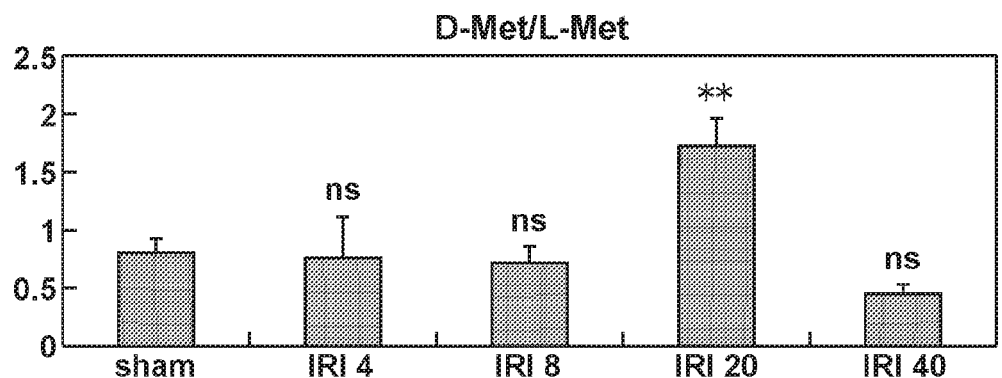
FIG. 5-O
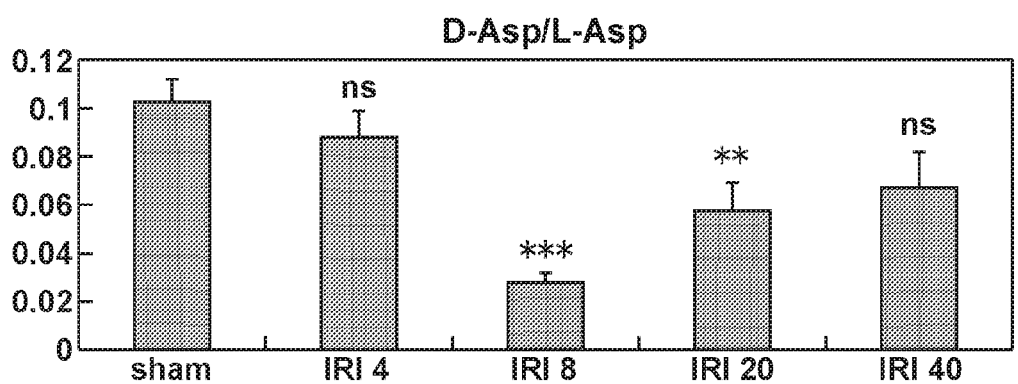
FIG. 5-P
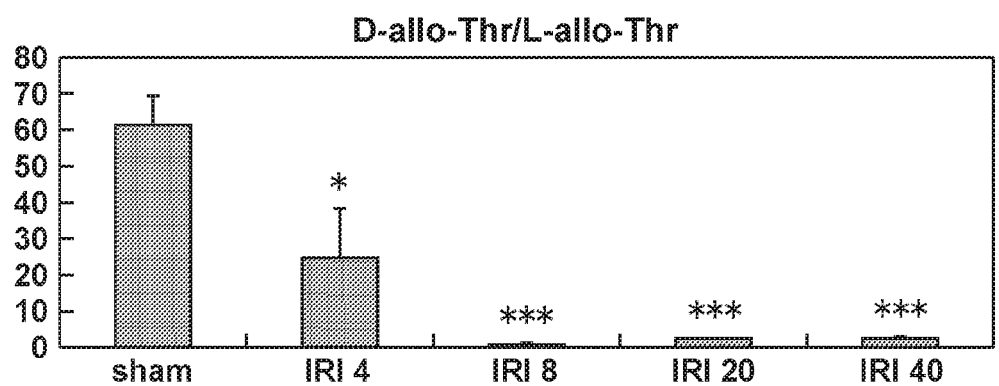
FIG. 5-Q

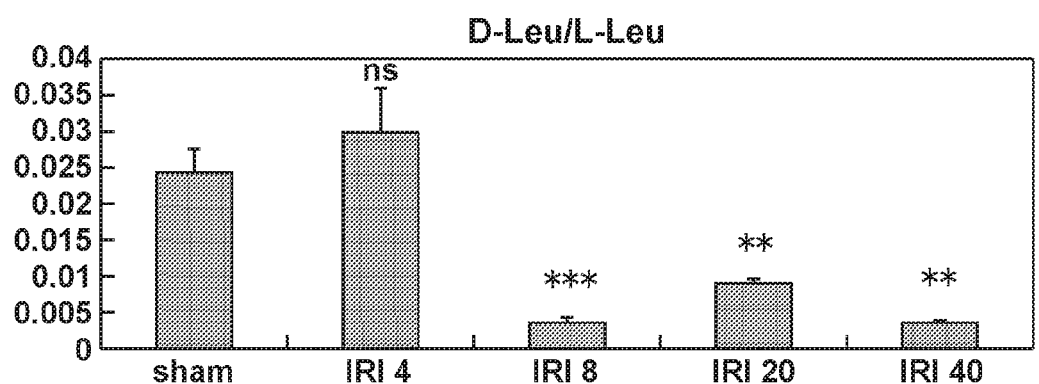
FIG. 5-R

MARKER FOR EARLY DIAGNOSIS OF KIDNEY FAILURE

CROSS-REFERENCE TO RELATED APPLICATIONS

This application is a National Stage application of PCT/JP2014/082899, filed Dec. 11, 2014, which claims priority from Japanese application JP 2013-256224, filed Dec. 11, 2013.

TECHNICAL FIELD

The present invention relates to a method for analyzing the blood or urine of a subject suspected of renal failure, and a system for analyzing a blood or urine sample of a subject suspected of renal failure. More particularly, the present invention relates to a method for analyzing the blood, plasma, serum or urine of a subject that comprises a step for measuring the concentration of a pair of D-form and L-form of at least one amino acid selected from the group consisting of [D-serine] and [L-serine] and the like in the blood, plasma, serum or urine of the subject, and to a system for analyzing a blood, plasma, serum or urine sample of the subject for performing the aforementioned analysis method, comprising a memory unit, an analysis and measurement unit, a data processing unit and a pathological information output unit.

BACKGROUND ART

Chronic kidney disease (CKD) is a disease that affects 13.3 million Japanese, corresponding to roughly 13% of the Japanese adult population, and threatens the health of Japanese citizens due to the risk of progressing to end stage kidney disease (ESKD). Chronic kidney disease includes all pathological states in which depressed renal function as represented by glomerular filtration rate is found, or findings suggesting kidney damage persist in a chronic state (three months or longer). There is no effective treatment method for chronic kidney disease, and if chronic kidney disease progresses resulting in further depression of renal function, there is the risk of uremia, resulting in the need for artificial dialysis or kidney transplant, which will place a considerable burden on the patient in terms of health care costs (Non-Patent Document 1). Chronic kidney disease does not exhibit subjective symptoms. Diagnosis using markers for early diagnosis of renal failure is necessary for early diagnosis of chronic kidney disease and inhibition of its progression. However, there is currently no biomarker that is satisfactory in terms of accurately reflecting the progression of renal dysfunction at an earlier stage than the occurrence of changes in renal function as represented by glomerular filtration rate.

An experimental animal model of acute kidney injury (AKI) is able to reproduce the early stages of renal dysfunction. Acute kidney injury is a disease in which renal function decreases rapidly over several weeks or several days. A known model of this disease is an acute kidney injury experimental model which is induced by a surgical procedure or administration of a drug. The "gold standards" for diagnosing acute kidney injury are urine production volume and serum creatinine concentration. Serum creatinine concentration is superior in that it can be evaluated without performing a biopsy regardless of the presence or absence of urination. However, glomerular filtration rate is required to be in a steady state. In a experimental animal model of acute kidney injury, which is not sensitive to small fluctuations in glomerular filtration rate, changes in glomerular filtration rate become apparent at a comparatively late stage. Since serum creatinine concentration also fluctuates due to conditions such as age, gender, muscle mass or medications being taken at the time, it cannot be a specific marker (Non-Patent Document 2). Reported examples of markers for acute kidney injury include neutrophil gelatinase-associated lipocalin (NGAL), interleukin-18 (IL-18), kidney injury molecule-1 (KIM-1), proteins such as fatty acid binding proteins or cystatin C, and metabolic low molecular weight compounds such as homovanillic acid sulfate or trimethylamine-N-oxide. However, none of these markers are detected in the early stage of renal failure.

Since concentrations of D-serine and D-alanine in the serum of renal failure patients are higher than serum concentrations in normal individuals, and both the D-form concentrations and ratio of D-form concentration/(D-form concentration+L-form concentration) correlate with creatinine, these amino acids have been suggested to be candidates for markers of renal proximal tubular dysfunction (Non-Patent Document 3). It is also disclosed that D-amino acids (Ala, Pro, Ser) in the serum of nephritis patients tend to be elevated and have a correlation with creatinine level (Non-Patent Document 9). In addition, D-alanine, D-serine, D-glutamic acid and D-aspartic acid are observed in the serum of renal failure patients, and because of this, measurement of serum D-alanine concentration has been suggested to be useful in the diagnosis of renal failure (Non-Patent Document 5). D-serine and D-alanine concentration in the urine along with the ratio of the D-form to the total of the D-form and L-form were investigated in healthy individuals of various age groups, and it was suggested that processing of D-serine in the kidneys is different (Non-Patent Document 6). Although one or more amino acids selected from the group consisting of D-serine, D-threonine, D-alanine, D-asparagine, D-allo-threonine, D-glutamine, D-proline and D-phenylalanine were disclosed as being able to be used as pathological indicators of kidney disease (Patent Document 1). However, even though it is described in this document that a body fluid such as blood, plasma or urine is used as a specimen, blood is the only specimen used to determine pathological indicators for kidney disease in the examples, while there is nothing disclosed as to whether or not amino acids present in urine can be used as pathological indicators of kidney disease. It is also disclosed that the D-form ratios of alanine, valine, proline, threonine, aspartic acid and asparagine increase significantly in the urine of renal failure patients, while there is no significant differences with respect to methionine and serine (Non-Patent Document 7). However, in this document, although the ratio of the D-form concentration/(D-form concentration+L-form concentration) of each amino acid is calculated in renal failure patients for which pathological assessment criteria have not been indicated, increases in these ratios are merely indicated randomly (or vaguely) irrespective of disease stage, and there are no descriptions or suggestions as to the fact that fluctuations in these ratios correlate with pathological or other biomarkers of renal failure. After the priority date of the present application, urinary D/L-serine ratio was suggested to be able to be used as a biomarker capable of detecting early stage ischemic renal failure and classifying pathological stage since it decreases over time following ischemia reperfusion injury (Non-Patent Document 8). D-amino acid oxidase, which is involved in the decomposition of D-amino acids, is expressed in renal proximal tubules, and the enzyme activity of D-amino acid oxidase is known to decrease in ischemia reperfusion model rats (Non-Patent Document 4). L-serine is reabsorbed while D-serine is hardly reabsorbed at all under physiological conditions. However, the manner in which D-serine and other D-amino acids fluctuate in the early stage of renal failure is unknown.

PRIOR ART DOCUMENTS

Patent Documents

Patent Document 1: International Publication No. WO 2013/140785

Non-Patent Documents

Non-Patent Document 1: KDIGO 2012, Clinical Practice Guideline for the Evaluation and Management of Chronic Kidney Disease, Kidney International Supplements 1 (2013)
Non-Patent Document 2: Slocum, J. L., et al, Transl. Res. 159: 277 (2012)
Non-Patent Document 3: Fukushima, T., et al, Biol. Pharm. Bull. 18: 1130 (1995)
Non-Patent Document 4: Zhang, H., et al, Amino Acids 42: 337 (2012)
Non-Patent Document 5: Ishida, et al, Kitasato Medical Journal, 23: 51-62 (1993)
Non-Patent Document 6: Yong Huang, et al, Biol. Pharm. Bull. 21: (2)156-162 (1998)
Non-Patent Document 7: Magdalena C. Waldhier et al, Chromatography B (2010) 1103-1112
Non-Patent Document 8: Jumpeji Sasabe et al, PLOS ONE, Vol. 9, Issue 1, e86504
Non-Patent Document 9: Nagata, Y., Viva Origino Vol. 18 (No. 2) (1990), 15th Academic Symposium, Collection of Abstracts

DISCLOSURE OF THE INVENTION

Problems to be Solved by the Invention

There is a need to develop a technology for diagnosis of early stage renal failure by identifying a biomarker of renal failure that can be collected from urine or blood and fluctuates at an earlier stage than glomerular filtration rate and serum creatinine concentration.

Means for Solving the Problems

The present invention provides a method for analyzing the blood or urine of a subject suspected of renal failure. The analysis method of the present invention comprises a step for measuring the concentration of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], and [D-lysine] and [L-lysine], and a step for calculating a pathological index value from the concentration of a pair of D-form and L-form of the at least one type of amino acid. Here, the pathological index value calculated from a pair of D-form and L-form amino acid enables to correlate a subject with the pathology of kidney disease in the case where a significant decrease in the proportion of the D-form is indicated. For example, the ratio of the concentration of the D-form to the concentration of the L-form of at least one amino acid, or the ratio or percentage of the concentration of the D-form to the sum of the concentrations of the D-form and the L-form, can be calculated as the pathological index value of the subject. Although amino acids in the urine of renal failure patients whose pathological assessment criteria have not been indicated are analyzed in Non-Patent Document 7, it is disclosed that the D-amino acid ratio for alanine, valine, proline, threonine and aspartic acid is significantly increased. Thus, a decrease in the proportion of D-amino acids in the urine of renal failure patients is a surprising finding.

In another mode of the analysis method of the present invention, [D-glutamine] and [L-glutamine], [D-threonine] and [L-threonine], [D-allo-threonine] and [L-allo-threonine] and [D-leucine] and [L-leucine] may be included in the aforementioned amino acid group. Thus, the analysis method of the present invention may comprise a step for measuring the concentration of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-alto-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], [D-lysine] and [L-lysine], [D-glutamine] and [L-glutamine], [D-threonine] and [L-threonine], [D-allo-threonine] and [L-allo-threonine], and [D-leucine] and [L-leucine], and a step for calculating a pathological index value from the concentration of a pair of D-form and L-form of the at least one amino acid. Here, the pathological index value calculated from a pair of D-form and L-form of at least one amino acid enables to correlate a subject with the pathology of kidney disease, when a significant decrease in the proportion of the D-form is indicated. For example, the ratio of the concentration of the D-form to the concentration of the L-form of at least one amino acids, or the ratio or percentage of the concentration of the D-form to the sum of the concentrations of the D-form and the L-form, can be calculated as the pathological index value of the subject.

Another mode of the present invention may also relate to a detection method for detecting renal failure, comprising a step for measuring the concentration of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], [D-lysine] and [L-lysine], [D-glutamine] and [L-glutamine], [D-threonine] and [L-threonine], [D-allo-threonine] and [L-allo-threonine], and [D-leucine] and [L-leucine] in the urine of a subject, and a step for calculating a pathological index value from the concentration of a pair of D-form and L-form of at least one amino acid that correlates a decrease in the proportion of a D-form with renal failure of the subject.

Here, the detection method relates to a method that may be performed by a non-physician such as a medical assistant or may be performed by an analysis facility.

Although an amino acid may be arbitrarily selected from the aforementioned amino acid group, it is more preferably selected from the group consisting of [D-histidine] and [L-histidine], [D-arginine] and [L-arginine], [D-glutamic acid] and [L-glutamic acid], [D-valine] and [L-valine], [D-allo-isoleucine] and [L-isoleucine], [D-lysine] and [L-lysine], [D-glutamine] and [L-glutamine], [D-leucine] and [L-leucine], and [D-allo-threonine] and [L-allo-threonine]. In another mode, each combination of amino acids may be excluded from the aforementioned amino acid group. For example, [D-serine] and [L-serine] may be excluded, [D-histidine] and [L-histidine] may be excluded, [D-asparagine] and [L-asparagine] may be excluded, [D-arginine] and [L-arginine] may be excluded, [D-allo-threonine] and [L-threonine] may be excluded, [D-glutamic acid] and [L-glutamic acid] may be excluded, [D-alanine] and [L-alanine] may be excluded, [L-proline] and [L-proline] may be excluded, [D-valine] and [L-valine] may be excluded, [D-allo-isoleucine] and [L-isoleucine] may be excluded, [D-phenylalanine] and [L-phenylalanine] may be excluded, [D-lysine] and [L-lysine] may be excluded, [D-glutamine] and [L-glutamine] may be excluded, [D-threonine] and [L-threonine] may be excluded, [D-allo-threonine] and [L-allo-threonine] may be excluded, and [D-leucine] and [L-leucine] may be excluded.

These pathological index values have been indicated to decrease following renal ischemia reperfusion in the same manner as urine creatinine concentration. Since a decrease in urine creatinine concentration indicates depression of renal function, it can be used as a marker of renal failure, and a pathological index value of the present application can also be used as a marker of renal failure in the same manner as urine creatinine concentration. Furthermore, urine renal failure markers in the form of KIM-1 and NGAL demonstrate increases in urine concentration in response to depressed renal function. In an experimental model of ischemia reperfusion, although urine creatinine concentration decreased significantly 8 hours after ischemia reperfusion, urine KIM-1 increases significantly 20 hours after ischemia reperfusion and urine NGAL increased significantly 8 hours after ischemia reperfusion (FIGS. 2-D, 2-F and 2-G). Since a pathological index value calculated using the concentration of a pair of D-form and L-form of one or more amino acids selected from the group consisting of [D-serine] and [L-serine], [D-histidine] and [L-histidine], [D-allo-threonine] and [L-allo-threonine], [D-asparagine] and [L-asparagine], [D-arginine] and [L-arginine], [D-alanine] and [L-alanine], [D-proline] and [L-proline], and [D-lysine] and [L-lysine] decreases significantly at a level of significance of $P<0.05$ 4 hours after renal ischemia reperfusion, it can be said to have higher sensitivity for renal failure. Thus, this pathological index value is preferably used from the viewpoint of having higher sensitivity for early stage renal failure. More preferably, since a pathological index value calculated using the concentration of a pair of D-form and L-form of one or more amino acids selected from the group consisting of [D-histidine] and [L-histidine], [D-asparagine] and [L-asparagine], [D-proline] and [L-proline], and [D-lysine] and [L-lysine] decreases significantly at a level of significance of $P<0.01$ 4 hours after renal ischemia reperfusion, this pathological index value can be used as a marker having higher sensitivity. Even more preferably, since a pathological index value calculated from concentration of a pair of D-form and L-form of one or more amino acids selected from the group consisting of [D-histidine] and [L-histidine], [D-proline] and [L-proline], and [D-lysine] and [L-lysine] decreases significantly at a level of significance of $P<0.001$ 4 hours after renal ischemia reperfusion, this pathological index value can be used as a marker having extremely high sensitivity. Thus, the pathological index value of the present invention has sensitivity that is equal to or higher than that of conventional renal failure markers such as serum creatinine, and can be used for early diagnosis of renal failure. Examples of early stage renal failure include a state in which serum creatinine has increased by 1.5 to 2.0 times, which is the criterion for the early stage of each of the RIFLE, AKIN and KDIGO classifications of acute kidney injury (AKI), a state wherein renal function reduction in chronic kidney disease (CKD) indicated by GFR is started, or an extremely early state prior to the appearance of changes in serum creatinine or GFR even though renal failure is present. In addition, a pathological index value calculated using the concentration of a pair of D-form and L-form of one or more amino acids selected from the group consisting of [D-glutamic acid] and [L-glutamic acid], [D-phenylalanine] and [L-phenylalanine], [D-valine] and [L-valine], [D-glutamine] and [L-glutamine], [D-threonine] and [L-threonine], [D-leucine] and [L-leucine], [D-allo-isoleucine] and [L-isoleucine], and [D-allo-threonine] and [L-threonine], which do not exhibit a significant difference 4 hours after renal ischemia reperfusion but exhibit a significant difference 8 hours after renal ischemia reperfusion, can be used as a marker having sensitivity equal to that of conventional markers such as creatinine.

The pathological index value calculated from the concentration of D-form and L-form of one amino acid may be used, or the pathological index value calculated from the concentration of another D-form and L-form of another amino acid can be used in combination therewith. For example, a pathological index value having extremely high sensitivity calculated from the concentration of D-form and L-form of one or more amino acids selected from the group consisting of [D-histidine] and [L-histidine], [D-proline] and [L-proline], and [D-lysine] and [L-lysine] may be combined with another pathological index value having extremely high sensitivity calculated from the concentration of a D-form and L-form of an amino acid selected from the same group. In addition, in a different mode, the aforementioned pathological index value having extremely high sensitivity can be used in combination with a pathological index value having a lower sensitivity, for example, a pathological index value calculated from the concentration of a D-form and L-form of one amino acid selected from the group consisting of [D-glutamic acid] and [L-glutamic acid], [D-phenylalanine] and [L-phenylalanine], [D-valine] and [L-valine], [D-glutamine] and [L-glutamine], [D-threonine] and [L-threonine], [D-leucine] and [L-leucine], [D-allo-isoleucine] and [L-isoleucine], and [D-alto-threonine] and [L-threonine], which enables sensitively detecting kidney injury in comparison with urine creatinine, urine KIM-1 or urine NGAL in a state in which depressed renal function, in which serum creatinine has increased by a factor of 1.5 to 2.0, has occurred or a state prior thereto.

The analysis method of the present invention may further comprise a step for determining whether the pathological index value of a subject is similar to the pathological index reference value of a healthy individual, whether the pathological index value of a subject is similar to the pathological index reference value of an acute renal failure patient or chronic renal failure patient, or whether the pathological index value of a subject is between the pathological index reference value of a healthy individual and the pathological index reference value of a chronic renal failure patient, by comparing the pathological index value of the subject with the pathological index reference value of a healthy individual and the pathological index reference value of an acute renal failure patient and/or chronic renal failure patient.

In still another mode, the present invention makes it possible to determine whether a subject suffers renal failure by preliminarily setting a threshold value based on the pathological index values of a healthy individual group and/or renal failure patient group, and then comparing the pathological index value of a subject with the threshold value. A person with ordinary skill in the art is able to suitably set a threshold value from the pathological index values of a healthy individual group and renal failure patient group. Although the average value, median value or X percentile value of the healthy individual group or renal failure patient group can be used for the threshold value, the threshold value is not limited thereto. Here, an arbitrary numerical value can be selected for X, and a value of 3, 5, 10, 15, 20, 30, 40, 60, 70, 80, 85, 90, 95 or 97 can be suitably used. Only one threshold value may be used or a plurality of threshold values can be set depending on the type of renal failure (acute or chronic), the cause thereof (such as drug-induced nephropathy, diabetic nephropathy, IgA nephropathy, membranous nephropathy or nephrosclerosis), disease state (early, intermediate or late) and the amino acids or combination thereof used. The pathology of the renal failure of a subject can be assessed, determined or diagnosed by comparing the pathological index value of the subject with a preset threshold value.

The analysis method of the present invention may further comprise a step for determining whether a first pathological index value of a subject, calculated from the concentration of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-allo-threonine] and [L-threonine], [D-alanine] and [L-alanine], [D-proline] and [L-proline], [D-valine] and [L-valine], and [D-lysine] and [L-lysine] in the blood, plasma, serum or urine of the subject, is between the pathological index reference value of a healthy individual and the pathological index reference value of a chronic renal failure patient, and whether the second pathological index value of the subject, calculated from the concentration of a pair of D-form and L-form of at least one amino acid among [D-glutamic] and [L-glutamic acid], [D-allo-isoleucine] and [L-isoleucine] and [D-phenylalanine] and [L-phenylalanine] in the blood, plasma, serum or urine of the subject, is between a pathological index reference value of the healthy individual and the pathological index reference value of the chronic renal failure patient.

In the present invention, the pathological index value of a subject calculated from the concentration of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-alanine] and [L-alanine], [D-proline] and [L-proline], and [D-lysine] and [L-lysine] can be used as a first pathological index value, while the pathological index value of the subject calculated from the concentration of a pair of D-form and L-form of at least one amino acid selected from the group consisting of [D-glutamic acid] and [L-glutamic acid], [D-allo-isoleucine] and [L-isoleucine], [D-phenylalanine] and [L-phenylalanine], [D-valine] and [L-valine], and [D-allo-threonine] and [L-threonine] can be used as a second pathological index value.

In the case [D-glutamine] and [L-glutamine], [D-threonine] and [L-threonine], [D-allo-threonine] and [L-allo-threonine] and [D-leucine] and [L-leucine] are included in the aforementioned amino acid group, the pathological index value of the subject calculated from the concentration of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-alanine] and [L-alanine], [D-proline] and [L-proline], [D-lysine] and [L-lysine], and [D-allo-threonine] and [L-allo-threonine] can be used for the first pathological index value. On the other hand, the pathological index value calculated from the concentration of a pair of D-form and L-form of at least one amino acid selected from the group consisting of [D-glutamine] and [L-glutamine], [D-threonine] and [L-threonine], and [D-leucine] and [L-leucine] in addition to [D-glutamic acid] and [L-glutamic acid], [D-allo-isoleucine] and [L-isoleucine], [D-phenylalanine] and [L-phenylalanine], and [D-valine and L-valine] can be used for the second pathological index value.

The present invention provides a system for analyzing a blood or urine sample of a subject suspected of renal failure. The sample analysis system of the present invention comprises a memory unit, an analysis and measurement unit, a data processing unit and a pathological information output unit. The aforementioned memory unit stores the pathological index reference values for the blood, plasma, serum or urine of healthy individuals, and the pathological index reference values for the blood, plasma, serum or urine of acute renal failure patients and/or chronic renal failure patients. The aforementioned analysis and measurement unit separates and quantifies at least one pair of amino acid stereoisomers present in the blood, plasma, serum or urine of the aforementioned subject selected from the group consisting of D-serine and L-serine, D-histidine and L-histidine, D-asparagine and L-asparagine, D-arginine and L-arginine, D-allo-threonine and L-threonine, D-glutamic acid and L-glutamic acid, D-alanine and L-alanine, D-proline and L-proline, D-valine and L-valine, D-allo-isoleucine and L-isoleucine, D-phenylalanine and L-phenylalanine, and D-lysine and L-lysine. The aforementioned data processing unit performs a step for calculating the pathological index value of the aforementioned subject from the concentration of a pair of D-form and L-form of at least one amino acid of the group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], and [D-lysine] and [L-lysine]. Here, the pathological index value calculated from the concentration of a pair of D-form and L-form of at least one amino acid enables a subject to be correlated with renal failure in the case of indicating a decrease in the composition ratio of the D-form.

In a different mode, D-glutamine and L-glutamine], D-threonine and L-threonine], [D-allo-threonine and L-allo-threonine and D-leucine and L-leucine may be included in addition to the aforementioned amino acid pairs. Thus, in a different mode, the aforementioned analysis and measurement unit separates and quantifies at least one pair of amino acid stereoisomers present in the blood, plasma, serum or urine of the aforementioned subject, selected from the group consisting of D-serine and L-serine, D-histidine and L-histidine, D-asparagine and L-asparagine, D-arginine and L-arginine, D-allo-threonine and L-threonine, D-glutamic acid and L-glutamic acid, D-alanine and L-alanine, D-proline and L-proline, D-valine and L-valine, D-allo-isoleucine and L-isoleucine, D-phenylalanine and L-phenylalanine, D-lysine and L-lysine, D-glutamine and L-glutamine, D-threonine and L-threonine, D-allo-threonine and L-allo-threonine and D-leucine and L-leucine. The aforementioned data processing unit performs a step for calculating the pathological index value of the aforementioned subject from the concentration of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], [D-lysine] and [L-lysine], [D-glutamine] and [L-glutamine], [D-threonine] and [L-threonine], [D-allo-threonine] and [L-allo-threonine] and [D-leucine] and [L-leucine]. Here, the pathological index value calculated from the concentration of a pair of D-form and L-form of at least one amino acid enables a subject to be correlated with renal failure in the case of indicating a decrease in the composition ratio of the D-form.

The pathological index value refers to a value that can be calculated from the concentration of a certain D-form and L-form of a certain amino acid, and enables a subject to be correlated with renal failure in the case of indicating a decrease in the composition ratio of the D-form. In the sample analysis system of the present invention, for example, in relation to a D-form and L-form pair, the ratio of the concentration of the D-form to the concentration of the L-form, and the ratio or percentage of the concentration of a D-form to the sum of the concentrations of the D-form and L-form, is defined as the pathological index value of a subject. When the pathological index value of the subject is compared with the pathological index reference value of a healthy individual and the pathological index reference value of a patient with acute renal failure and/or chronic renal failure, and the pathological index value of the subject is similar to the pathological index reference value of the healthy individual, information that the aforementioned subject is hardly suspected of renal failure is defined as pathological information of the aforementioned subject. When the pathological index value of the aforementioned subject is similar to the pathological index reference value of the aforementioned chronic renal failure patient, information that the aforementioned subject is suspected of renal failure is defined as pathological information of the aforementioned subject. When the pathological index value of the aforementioned subject is between the pathological index reference value of the aforementioned healthy individual and the pathological index reference value of the aforementioned chronic renal failure patient, information that the aforementioned subject is suspected of early stage renal failure is defined as pathological information of the aforementioned subject. The aforementioned pathological information output unit outputs the pathological information of the aforementioned subject.

In the sample analysis system of the present invention, when a first pathological index value of a subject calculated from the concentration in the blood, plasma, serum or urine of the aforementioned subject of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-alto-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], and [D-lysine] and [L-lysine] is between the pathological index reference value of the aforementioned healthy individual and the pathological index reference value of the aforementioned chronic renal failure patient, and a second pathological index value of the aforementioned subject calculated from the concentration in the blood, plasma, serum or urine of the aforementioned subject of a pair of D-form and L-form of at least one amino acid selected from the group consisting of [D-glutamic acid] and [L-glutamic acid], [D-allo-isoleucine] and [L-isoleucine], and [D-phenylalanine] and [L-phenylalanine] is between the pathological index reference value of the aforementioned healthy individual and the pathological index reference value of the aforementioned chronic renal failure patient, information that the aforementioned subject is suspected of extremely early stage renal failure is defined as pathological information of the aforementioned subject.

The present invention provides a method for diagnosing renal failure. The diagnostic method of the present invention comprises a step for measuring the concentration in the blood, plasma, serum or urine of a subject suspected of renal failure of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], and [D-lysine] and [L-lysine], and a step for calculating a pathological index value from the aforementioned concentration of the pair of D-form and L-form of aforementioned at least one amino acid.

In a different mode of the diagnostic method of the present invention, [D-glutamine] and [L-glutamine], [D-threonine] and [L-threonine], and [D-leucine] and [L-leucine] may be included in the aforementioned amino acid group. Thus, the diagnostic method of the present invention comprises a step for measuring the concentration in the blood, plasma, serum or urine of a subject suspected of renal failure of a pair of D-form and L-form of at least one amino acid selected from the amino acid group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], [D-lysine] and [L-lysine], [D-glutamine] and [L-glutamine], [D-threonine] and [L-threonine], and [D-leucine] and [L-leucine], and a step for calculating a pathological index value from the aforementioned concentration of the pair of D-form and L-form of aforementioned at least one amino acid.

Here, the pathological index value calculated from the concentration of a pair of D-form and L-form of at least one amino acid enables a subject to be correlated with renal failure in the case of indicating a decrease in the composition ratio of the D-form. The ratio of the concentration of the D-form to the concentration of the L-form of at least one amino acid pair, or the ratio or percentage of the concentration of the D-form to the sum of the concentrations of D-form and L-form, can be used as the pathological index value of the aforementioned subject.

The diagnostic method of the present invention may further comprise a step for diagnosing that the aforementioned subject has a high likelihood of being a healthy individual or is hardly suspected of renal failure when the pathological index value of the aforementioned subject is compared with the pathological index reference value of the healthy individual and the pathological index reference value of a patient with acute renal failure and/or chronic renal failure, and the pathological index value of the aforementioned subject is similar to the pathological index reference value of the healthy individual; the aforementioned subject is diagnosed as being strongly suspected of renal failure when the pathological index value of the aforementioned subject is similar to the pathological index reference value of the aforementioned patient having acute renal failure or chronic renal failure; and the aforementioned subject is diagnosed as being suspected of early stage renal failure when the pathological index value of the aforementioned subject is between the pathological index reference value of the healthy individual and the pathological index reference value of the patient having acute renal failure or chronic renal failure.

The diagnostic method of the present invention comprises a step for diagnosing that a subject is suspected of extremely early stage renal failure when a first pathological index value of a subject calculated from the concentration in the blood, plasma, serum or urine of the aforementioned subject of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-allo-threonine] and [L-threonine], [D-alanine] and [L-alanine], [D-proline] and [L-proline], [D-valine] and [L-valine], and [D-lysine] and [L-lysine] is between the pathological index reference value of the aforementioned healthy individual and the pathological index reference value of the aforementioned chronic renal failure patient, and a second pathological index value of the aforementioned subject calculated from the concentration in the blood, plasma, serum or urine of the aforementioned subject of a pair of D-form and L-form of at least one amino acid selected from the group consisting of [D-glutamic acid] and [L-glutamic acid], [D-allo-isoleucine] and [L-isoleucine], and [D-phenylalanine] and [L-phenylalanine] is between the pathological index reference value of the aforementioned healthy individual and the pathological index reference value of the aforementioned chronic renal failure patient.

The present invention provides a method for treating renal failure. The treatment method of the present invention comprises a step for measuring the concentration in the blood, plasma, serum or urine of a subject suspected of renal failure of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-allo-threonine] and [L-threonine], [D-glutamic acid] and [L-glutamic acid], [D-alanine] and [L-alanine], [D-proline] and [L-proline], [D-valine] and [L-valine], [D-allo-isoleucine] and [L-isoleucine], [D-phenylalanine] and [L-phenylalanine], and [D-lysine] and [L-lysine], a step for calculating a pathological index value from the aforementioned concentration of a pair of D-form and L-form of at least one amino acid, a step for diagnosing that the aforementioned subject has a high likelihood of being a healthy individual or is hardly suspected of renal failure when the pathological index value of the aforementioned subject is compared with the pathological index reference value of the healthy individual and the pathological index reference value of a patient with acute renal failure and/or chronic renal failure and the pathological index value of the aforementioned subject is similar to the pathological index reference value of the healthy individual, the aforementioned subject is diagnosed as being strongly suspected of renal failure when the pathological index value of the aforementioned subject is similar to the pathological index reference value of the aforementioned patient having acute renal failure or chronic renal failure, and the aforementioned subject is diagnosed has being suspected of early stage renal failure when the pathological index value of the aforementioned subject is between the pathological index reference value of the healthy individual and the pathological index reference value of the patient having acute renal failure or chronic renal failure, and a step for treating the aforementioned subject when the aforementioned subject has been diagnosed as being strongly suspected of renal failure by administering a therapeutic drug that inhibits the progression or improves renal failure, including antihypertensive drugs including, but not limited to, angiotensin-converting enzymes and angiotensin II receptor antagonists, antidiabetic drugs including, but not limited to, α-glucosidase inhibitors and insulin preparations, antidyslipidemic drugs including, but not limited to, HMG-CoA reductase inhibitors and intestinal cholesterol transporter inhibitors, antianemic drugs including, but not limited to, recombinant human erythropoietin preparations, therapeutic drugs for bone and mineral metabolic disorders, therapeutic drugs for hyperuricemia, and therapeutic drugs for uremic toxins including, but not limited to, spherical adsorbent carbon medications.

The treatment method of the present invention comprises a step for diagnosing that a subject is suspected of extremely early stage renal failure when a first pathological index value of the aforementioned subject calculated from the concentration in the blood, plasma, serum or urine of the aforementioned subject of a pair of D-form and L-form of at least one amino acid selected from the group consisting of [D-serine] and [L-serine], [D-histidine] and [L-histidine], [D-asparagine] and [L-asparagine], [D-arginine] and [L-arginine], [D-allo-threonine] and [L-threonine], [D-alanine] and [L-alanine], [D-proline] and [L-proline], [D-valine] and [L-valine], and [D-lysine] and [L-lysine] is between the pathological index reference value of the aforementioned healthy individual and the pathological index reference value of the aforementioned chronic renal failure patient, and a second pathological index value of the aforementioned subject calculated from the concentration in the blood, plasma, serum or urine of the aforementioned subject of a pair of D-form and L-form of at least one amino acid selected from [D-glutamic acid] and [L-glutamic acid], [D-allo-isoleucine] and [L-isoleucine], and [D-phenylalanine] and [L-phenylalanine] is between the pathological index reference value of the aforementioned healthy individual and the pathological index reference value of the aforementioned chronic renal failure patient, and a step for treating the aforementioned subject by administering a therapeutic drug for hyperkalemia, including, but not limited to, sodium polystyrene sulfonate, and a therapeutic drug for hyperphosphatemia, including, but not limited to, calcium carbonate and calcium acetate.

Measurement of D-amino acid concentration in blood, plasma, serum or urine in the present invention may be performed using any method commonly known among persons with ordinary skill in the art. For example, a method consisting of preliminarily stereospecifically derivatizing D- and L-amino acids with o-phthaldehyde (OPA), N-tert-butyloxycarbonyl-L-cysteine (Boc-L-Cys) or other modifying reagent, followed by separating a mixture of 100 mM acetate buffer (pH 6.0) and acetonitrile by gradient elution using an analytical column in the manner of ODS-80TsQA can be used to simultaneous measure the D-forms and L-forms of aspartic acid, serine and alanine. In addition, a method consisting of preliminarily derivatizing D- and L-amino acids with a fluorescent reagent in the manner of 4-fluoro-7-nitro-2,1,3-benzoxadiazole (NBD-F) and then stereospecifically separating each amino acid using an analytical column in the manner of ODS-80TsQA or Mightysil RP-18GP, followed by stereospecifically separating by optically resolving using a Pirkle chiral stationary phase column (such as the Sumichiral OA-2500S or R), can be used to measure trace amounts of proline, leucine and other amino acids (Hamase, K. and Zaitsu, K.: Analytical Chemistry, Vol. 53, 677-690 (2004)). An optical resolution column system in the present description refers to a separation analysis system that at least uses an optical resolution column, and may include separation analyses using an analytical column other than an optical resolution column. More specifically, the concentrations of D- and L-amino acids in a sample can be measured by using an optical isomer analysis method comprising a step for passing a sample containing components having optical isomers through a stationary phase in the form of a first column packing material together with a mobile phase in the form of a first liquid to separate the aforementioned components of the aforementioned sample, a step for individually retaining each of the aforementioned components of the aforementioned sample in a multi-loop unit, a step for supplying each of the aforementioned components of the aforementioned sample individually retained in the aforementioned multi-loop unit by passing the flow path through a stationary phase in the form of a second column packing material having an optically active center together with a mobile phase in the form of a second liquid to resolve the aforementioned optical isomers contained in each component of the aforementioned sample, and a step for detecting the aforementioned optical isomers contained in each component of the aforementioned sample (Japanese Patent No. 4291628). Alternatively, D-amino acids can be quantified by an immunochemical method that uses monoclonal antibodies that identify optical isomers of amino acids, such as a monoclonal antibody that specifically binds to D-leucine or D-asparagine and the like (Japanese Patent Application No. 2008-27650).

In the present description, notations of amino acids enclosed in brackets ([ ]) (such as [D-serine]) refer to the concentration of that amino acid. In the present invention, the ratio of the concentration of a D-form to the concentration of an L-form and the percentage of the concentration of a D-form to the sum of the concentrations of a D-form and an L-form, for example, are used as parameters (pathological index values) based on the concentration of an amino acid. The volume of a liquid in the manner of blood, serum, plasma or urine is reduced in order to divide the concentration of a certain substance by the concentration of another substance. Consequently, differing from the case of concentration, these parameters offer the advantage of eliminating the need for correction for liquid volume.

In the present invention, the function of the kidneys, which produce urine by specifically removing only a portion of the components in blood by filtering and reabsorbing blood, play an important role. Consequently, although amino acid concentrations in the present invention may differ greatly between blood and urine, the differences between blood, serum and plasma are not that large. This is because amino acids are not known to be specifically concentrated in blood cells or blood clots and the like. Therefore, although serum concentrations are measured in examples of the present invention and parameters based on serum concentrations are used for the pathological index values of subjects or the pathological index reference values of healthy individuals and renal failure patients, blood concentrations or plasma concentrations may be measured instead of serum concentrations, and parameters based on blood concentrations or plasma concentrations may be used for the pathological index values of subjects and the pathological index reference values of healthy individuals and renal failure patients.

In the present description, a "pathological index value" refers to a numerical value able to be calculated based on the concentrations of a plurality of biomarkers and not on the concentration of individual biomarker molecules. A pathological index value used in the present description can be calculated from the concentration of a certain D-form and L-form of at least one amino acid//, and refers to a value that enables a subject to be correlated with renal failure in the case of indicating a decrease in the composition ratio of the D-form. Pathological index values include, but are not limited to, the concentration ratio between a certain amino acid and an enantiomer thereof, such as the ratio of the concentration of a D-form to the concentration of the L-form of a certain amino acid, and the percentage of the concentration of a D-form to the sum of the concentrations of the D-form and L-form.

In the present description, a "pathological index reference value" refers to the average value or median value of the pathological index value of a biomarker molecule obtained for healthy individuals and acute renal failure and/or chronic renal failure patients diagnosed by a known diagnostic technique. Although a pathological index value is a numerical value of a specific subject at a specific point in time, a pathological index reference value is a numerical value obtained by statistical processing from a plurality of healthy individuals and patients with acute renal failure and/or chronic renal failure. Thus, a certain pathological index value being similar to a certain pathological index reference value refers to the absence of a significant difference between the pathological index value and the aforementioned pathological index reference value. For example, a statistical technique such as the two-tailed Student's t-test, one-way analysis of variance or Tukey's multiple comparison test can be used. In addition, a significance threshold P value of less than 0.05 constitutes significance in these tests.

The system for analyzing the blood, plasma, serum or urine of a subject in the present invention comprises a memory unit, analysis and measurement unit, data processing unit and pathological information output unit. Here, the memory unit contains memory that stores pathological index reference values, obtained from parameters based on enantiomer concentration data of amino acids present in blood, plasma, serum or urine, obtained for healthy individuals and patients with acute renal failure and/or chronic renal failure diagnosed by a known diagnostic technique. The aforementioned storage unit may contain significance threshold P data obtained by statistical processing from the number of the aforementioned healthy individuals and patients and individual data. The aforementioned analysis and measurement unit contains an automated analyzer, capable of automatically operating a two-dimensional HPLC system by remote control that measures amino acid enantiomer concentration explained in the present description, and a central control device for controlling the automated analyzer. The aforementioned data processing unit calculates parameters explained in the present description from amino acid enantiomer concentrations obtained with the aforementioned analysis and measurement unit. This unit also compares a pathological index value of a subject obtained from these parameters with pathological index reference values of healthy individuals and patients recalled from the aforementioned memory unit. When the pathological index value of the aforementioned subject is similar to the pathological index reference value of the aforementioned healthy individuals, information that the aforementioned subject is weakly suspected of renal failure is defined as pathological information of the aforementioned subject. When the pathological index value of the aforementioned subject is similar to the pathological index reference value of the aforementioned chronic renal failure patients, information that the aforementioned subject is suspected of renal failure is defined as pathological information of the aforementioned subject. When the pathological index value of the aforementioned subject is between the pathological index reference value of the aforementioned healthy individuals and the pathological index reference value of the aforementioned chronic renal failure patients, information that the aforementioned subject is suspected of early stage renal failure is defined as pathological information of the aforementioned subject. At this time, the aforementioned significance threshold P value may be recalled from the aforementioned memory unit and used to determine the degree to which the pathological index value of the aforementioned subject is similar to the pathological index reference value of the aforementioned healthy individuals or patients. The data processing unit contains a computer of the prior art and pathological information processing software stored in the computer. The aforementioned pathological information output unit may display the pathological information of the aforementioned subject on a liquid crystal or other display screen, output the information to a printer for printout, or transmit the pathological information of the subject via the Internet or LAN and the like as data.

In the present invention, analyzed or detected renal failure refers to a state in which renal function is depressed below that when normal, and includes all forms of kidney damage used in the normal sense of the word. Although not limited thereto, renal failure generally refers to a state in which renal function is below 30% of normal renal function, and is broadly classified into acute renal failure and chronic renal failure. Examples of the causes of depressed renal function include multiple factors such as immune system abnormalities or drug allergies, hypertension, diabetes, hemorrhage or sudden drop in blood pressure, infection or dehydration accompanying burns. Classifications of disease stage in the manner of the RIFLE classification, AKIN classification or KDIGO classification have been advocated for acute renal failure (AKI), and acute renal failure has been classified as risk (stage 1), injury (stage 2) and failure (stage 3), and as loss and end-stage kidney disease corresponding to the duration thereof. These classifications all use serum creatinine level and urine volume as indicators, and the diagnostic criterion in the case of risk (stage 1), for example, consists of a 1.5-fold to 2.0-fold increase in serum creatinine from the baseline or urine volume of less than 0.5 ml/kg/hr persisting for 6 hours or more, that in the case of injury (stage 2) consists of a 2.0-fold to 3.0-fold increase in serum creatinine from the baseline or urine volume of less than 0.5 ml/kg/hr persisting for 12 hours or more, while that in the case of failure (stage 3) consists of a 3.0-fold or more increase in serum creatinine from the baseline or urine volume of less than 0.3 ml/kg/hr persisting for 24 hours or more. On the other hand, these classifications are able to more accurately classify acute renal failure by using in combination with other indicators such as the amount of change in GFR. Diagnostic criteria for disease stage 1 (normal renal function although kidney damage is present, eGFR≥90) to disease stage 5 (renal failure, eGFR<15) are indicated for chronic kidney disease (CKD) in guidelines of the Japanese Society of Nephrology (2009). Here, estimated glomerular filtration rate (eGFR), used as an indicator, is calculated with serum creatinine level based on age and gender, and indicates the capacity of the kidney to discharge body waste into urine. In the analysis and test method of the present invention, depression of renal function can be detected with higher sensitivity than conventional renal function markers. Thus, subjects can be classified into a risk group that was not classified as renal failure using conventional markers, and for example, depression of renal function can even be detected in a high risk group having risk factors for AKI or CKD in the manner of the previously described causes, but for which there are no well-defined fluctuations observed for serum creatinine or GFR.

In the present invention, the subject is not limited to a human, but rather can include experimental animals such as mice, rats, rabbits, dogs or monkeys. Thus, a subject may also be represented as a subject.

The analysis method of the present invention can be used to gather preliminary data for a method for diagnosing chronic renal failure and/or acute renal failure. Although a physician can diagnose chronic renal failure and/or acute renal failure using such preliminary data, this analysis method may also be performed by a non-physician such as a medical assistant, or can be performed by an analysis facility and the like. Thus, the analysis method of the present invention can also be said to be a preliminary diagnostic method.

All documents mentioned in the present description are incorporated in their entirety in the present description by reference.

BRIEF DESCRIPTION OF THE DRAWINGS

FIG. 1-A is a typical chromatogram obtained by two-dimensional HPLC of D-/L-serine in the serum of C57BL/6J wild-type mice that underwent sham surgery or ischemia reperfusion treatment.

FIG. 1-B is a graph showing changes in D-serine concentration in the serum of C57BL/6J wild-type mice that underwent renal ischemia reperfusion treatment.

FIG. 1-C is a graph showing changes in L-serine concentration in the serum of C57BL/6J wild-type mice that underwent renal ischemia reperfusion treatment.

FIG. 1-D is a graph showing changes in the ratio of D-serine concentration to L-serine concentration in the serum of C57BL/6J wild-type mice that underwent renal ischemia reperfusion treatment.

FIG. 1-E is a graph showing changes in creatinine concentration in the serum of C57BL/6J wild-type mice that underwent renal ischemia reperfusion treatment.

FIG. 1-F is a graph showing changes in cystatin C concentration in the serum of C57BL/6J wild-type mice that underwent renal ischemia reperfusion treatment.

FIG. 2-A is a typical chromatogram obtained by two-dimensional HPLC of D-/L-serine concentration in the urine of C57BL/6J wild-type mice that underwent sham surgery and ischemia reperfusion treatment.

FIG. 2-B is a graph showing changes in D-serine concentration in the urine of C57BL/6J wild-type mice that underwent renal ischemia reperfusion treatment.

FIG. 2-C is a graph showing changes in L-serine concentration urine of C57BL/6J wild-type mice that underwent renal ischemia reperfusion treatment.

FIG. 2-D is a graph showing changes in creatinine concentration urine of C57BL/6J wild-type mice that underwent renal ischemia reperfusion treatment.

FIG. 2-E is a graph showing changes in the ratio of D-serine concentration to L-serine concentration urine of C57BL/6J wild-type mice that underwent renal ischemia reperfusion treatment.

FIG. 2-F is a graph showing changes in KIM-1 concentration urine of C57BL/6J wild-type mice that underwent renal ischemia reperfusion treatment.

FIG. 2-G is a graph showing changes in NGAL concentration urine of C57BL/6J wild-type mice that underwent renal ischemia reperfusion treatment.

FIG. 3-A is a graph showing changes in the ratio of D-histidine concentration to L-histidine concentration in the urine of C57BL/6J wild-type mice that underwent renal ischemia reperfusion treatment.

FIG. 3-B is a graph showing changes in the ratio of D-asparagine concentration to L-asparagine concentration in the urine of C57BL/6J wild-type mice that underwent renal ischemia reperfusion treatment.

FIG. 3-C is a graph showing changes in the ratio of D-serine concentration to L-serine concentration in the urine of C57BL/6J wild-type mice that underwent renal ischemia reperfusion treatment.

FIG. 3-D is a graph showing changes in the ratio of D-arginine concentration to L-arginine concentration in the urine of C57BL/6J wild-type mice that underwent renal ischemia reperfusion treatment.

FIG. 3-E is a graph showing changes in the ratio of D-allo-threonine concentration to L-threonine concentration in the urine of C57BL/6J wild-type mice that underwent renal ischemia reperfusion treatment.

FIG. 3-F is a graph showing changes in the ratio of D-glutamic acid concentration to L-glutamic acid concentration in the urine of C57BL/6J wild-type mice that underwent renal ischemia reperfusion treatment.

FIG. 3-G is a graph showing changes in the ratio of D-alanine concentration to L-alanine concentration in the urine of C57BL/6J wild-type mice that underwent renal ischemia reperfusion treatment.

FIG. 3-H is a graph showing changes in the ratio of D-proline concentration to L-proline concentration in the urine of C57BL/6J wild-type mice that underwent renal ischemia reperfusion treatment.

FIG. 3-I is a graph showing changes in the ratio of D-valine concentration to L-valine concentration in the urine of C57BL/6J wild-type mice that underwent renal ischemia reperfusion treatment.

FIG. 3-J is a graph showing changes in the ratio of D-allo-isoleucine concentration to L-isoleucine concentration in the urine of C57BL/6J wild-type mice that underwent renal ischemia reperfusion treatment.

FIG. 3-K is a graph showing changes in the ratio of D-phenylalanine concentration to L-phenylalanine concentration in the urine of C57BL/6J wild-type mice that underwent renal ischemia reperfusion treatment.

FIG. 3-L is a graph showing changes in the ratio of D-lysine concentration to L-lysine concentration in the urine of C57BL/6J wild-type mice that underwent renal ischemia reperfusion treatment.

FIG. 4-A is a graph showing changes in the percentage of D-histidine concentration to the sum of L-histidine concentration and D-histidine concentration in the urine of C57BL/6J wild-type mice that underwent renal ischemia reperfusion treatment.

FIG. 4-B is a graph showing changes in the percentage of D-asparagine concentration to the sum of L-asparagine concentration and D-asparagine concentration in the urine of C57BL/6J wild-type mice that underwent renal ischemia reperfusion treatment.

FIG. 4-C is a graph showing changes in the percentage of D-serine concentration to the sum of L-serine concentration and D-serine concentration in the urine of C57BL/6J wild-type mice that underwent renal ischemia reperfusion treatment.

FIG. 4-D is a graph showing changes in the percentage of D-arginine concentration to the sum of L-arginine concentration and D-arginine concentration in the urine of C57BL/6J wild-type mice that underwent renal ischemia reperfusion treatment.

FIG. 4-E is a graph showing changes in the percentage of D-allo-threonine concentration to the sum of L-threonine concentration and D-allo-threonine concentration in the urine of C57BL/6J wild-type mice that underwent renal ischemia reperfusion treatment.

FIG. 4-F is a graph showing changes in the percentage of D-glutamic acid concentration to the sum of L-glutamic acid concentration and D-glutamic acid concentration in the urine of C57BL/6J wild-type mice that underwent renal ischemia reperfusion treatment.

FIG. 4-G is a graph showing changes in the percentage of D-alanine concentration to the sum of L-alanine concentration and D-alanine concentration in the urine of C57BL/6J wild-type mice that underwent renal ischemia reperfusion treatment.

FIG. 4-H is a graph showing changes in the percentage of D-proline concentration to the sum of L-proline concentration and D-proline concentration in the urine of C57BL/6J wild-type mice that underwent renal ischemia reperfusion treatment.

FIG. 4-I is a graph showing changes in the percentage of D-valine concentration to the sum of L-valine concentration and D-valine concentration in the urine of C57BL/6J wild-type mice that underwent renal ischemia reperfusion treatment.

FIG. 4-J is a graph showing changes in the percentage of D-allo-isoleucine concentration to the sum of L-isoleucine concentration and D-allo-isoleucine concentration in the urine of C57BL/6J wild-type mice that underwent renal ischemia reperfusion treatment.

FIG. 4-K is a graph showing changes in the percentage of D-phenylalanine concentration to the sum of L-phenylalanine concentration and D-phenylalanine concentration in the urine of C57BL/6J wild-type mice that underwent renal ischemia reperfusion treatment.

FIG. 4-L is a graph showing changes in the percentage of D-lysine concentration to the sum of L-lysine concentration and D-lysine concentration in the urine of C57BL/6J wild-type mice that underwent renal ischemia reperfusion treatment.

FIG. 5-A is a graph showing changes in the ratio of D-histidine concentration to L-histidine concentration in the urine of C57BL/6J wild-type mice that underwent renal ischemia reperfusion treatment.

FIG. 5-B is a graph showing changes in the ratio of D-asparagine concentration to L-asparagine concentration in the urine of C57BL/6J wild-type mice that underwent renal ischemia reperfusion treatment.

FIG. 5-C is a graph showing changes in the ratio of D-serine concentration to L-serine concentration in the urine of C57BL/6J wild-type mice that underwent renal ischemia reperfusion treatment.

FIG. 5-D is a graph showing changes in the ratio of D-arginine concentration to L-arginine concentration in the urine of C57BL/6J wild-type mice that underwent renal ischemia reperfusion treatment.

FIG. 5-E is a graph showing changes in the ratio of D-allo-threonine concentration to L-threonine concentration in the urine of C57BL/6J wild-type mice that underwent renal ischemia reperfusion treatment.

FIG. 5-F is a graph showing changes in the ratio of D-glutamic acid concentration to L-glutamic acid concentration in the urine of C57BL/6J wild-type mice that underwent renal ischemia reperfusion treatment.

FIG. 5-G is a graph showing changes in the ratio of D-alanine concentration to L-alanine concentration in the urine of C57BL/6J wild-type mice that underwent renal ischemia reperfusion treatment.

FIG. 5-H is a graph showing changes in the ratio of D-proline concentration to L-proline concentration in the urine of C57BL/6J wild-type mice that underwent renal ischemia reperfusion treatment.

FIG. 5-I is a graph showing changes in the ratio of D-valine concentration to L-valine concentration in the urine of C57BL/6J wild-type mice that underwent renal ischemia reperfusion treatment.

FIG. 5-J is a graph showing changes in the ratio of D-allo-isoleucine concentration to L-isoleucine concentration in the urine of C57BL/6J wild-type mice that underwent renal ischemia reperfusion treatment.

FIG. 5-K is a graph showing changes in the ratio of D-phenylalanine concentration to L-phenylalanine concentration in the urine of C57BL/6J wild-type mice that underwent renal ischemia reperfusion treatment.

FIG. 5-L is a graph showing changes in the ratio of D-lysine concentration to L-lysine concentration in the urine of C57BL/6J wild-type mice that underwent renal ischemia reperfusion treatment.

FIG. 5-M is a graph showing changes in the ratio of D-glutamine concentration to L-glutamine concentration in the urine of C57BL/6J wild-type mice that underwent renal ischemia reperfusion treatment.

FIG. 5-N is a graph showing changes in the ratio of D-threonine concentration to L-threonine concentration in the urine of C57BL/6J wild-type mice that underwent renal ischemia reperfusion treatment.

FIG. 5-O is a graph showing changes in the ratio of D-methionine concentration to L-methionine concentration in the urine of C57BL/6J wild-type mice that underwent renal ischemia reperfusion treatment.

FIG. 5-P is a graph showing changes in the ratio of D-aspartic acid concentration to L-aspartic acid concentration in the urine of C57BL/6J wild-type mice that underwent renal ischemia reperfusion treatment.

FIG. 5-Q is a graph showing changes in the ratio of D-allo-threonine concentration to L-allo-threonine concentration in the urine of C57BL/6J wild-type mice that underwent renal ischemia reperfusion treatment.

FIG. 5-R is a graph showing changes in the ratio of D-leucine concentration to L-leucine concentration in the urine of C57BL/6J wild-type mice that underwent renal ischemia reperfusion treatment.

BEST MODE FOR CARRYING OUT THE INVENTION

Examples of the present invention explained below are only intended to be exemplary and do not limit the technical scope of the present invention. The technical scope of the present invention is limited only by the description of the scope of claim for patent. The present invention can be modified, such as by adding, deleting or substituting constituent features of the present invention, under the condition that such modifications do not deviate from the gist of the present invention.

Example 1

1. Materials and Methods
(1) Research Ethics
All experiments were performed in accordance with facility guidelines and were approved by the animal experimentation ethics committee of the facility.
(2) Materials
Amino acid enantiomers and HPLC-grade acetonitrile were purchased from Nacalai Tesque, Inc., Kyoto, Japan. HPLC-grade methanol, trifluoroacetic acid and boric acid were purchased from Wako Pure Chemical Industries, Ltd., Osaka, Japan. Water was purified using the Milli-Q Gradient A10 System.
(3) Animals
Animals were housed in an SPF environment under a light/dark cycle of 12 hours each while allowing unrestricted access to water and feed. C57BL/6J mice were purchased from CLEA Japan, Inc., Tokyo, Japan. Mice having a point mutation of D-amino acid oxidase used in the examples were the result of a mutation in which glycine at position 181 was replaced with arginine and obtained by backcrossing strain ddY mice to strain C57BL/6J mice (Sasabe, J. et al, Proc. Natl. Acad. Sci. U.S.A., 109:627 (2012)). Serine racemase knockout mice were produced according to Miyoshi, Y. et al (Amino Acids 43:1919 (2012)).
(4) Renal Ischemia Reperfusion Treatment
12- to 16-week old male mice were subjected to renal ischemia reperfusion injury (IRI). The right kidney was removed under pentobarbital anesthesia prior to IRI treatment. Mice were randomly selected after 12 days and subjected to a sham surgery or IRI treatment. The left kidney was placed outside the body and the arteries and veins were occluded with clamps (Schwartz Micro Serrefines, Fine Science Tools Inc., Vancouver, Canada). Blood circulation was resumed 45 minutes later and the clamps were removed. The return of the surface of the kidney to its original color was confirmed visually after which the kidney was returned to the body. Although the left kidney was placed outside the body in the sham surgery, occlusion of blood flow by clamping was not performed. The mice were anesthetized with diethyl ether, blood was collected from the vena cava, and urine was collected from the urinary bladder after reperfusing for 4, 8, 20 and 24 hours. Following excision, the kidneys were perfused and fixed as necessary. Serum was separated by centrifuging at 1500×g for 10 minutes in a Becton Dickinson (BD) Microtainer. Serum and urine creatinine levels and blood urea nitrogen (BUN) levels were measured using the Fuji DRI-CHEM4000 System (Fujifilm Corp., Tokyo, Japan).

Serum cystatin C levels and urine KIM-1 and NGAL levels were measured using a mouse ELISA kit available from R&D Systems, Inc.

(5) Complete Analysis of Amino Acid Stereoisomers

The aforementioned samples were subjected to complete analysis of amino acid stereoisomers using the D/L-Amino Acid Simultaneous High-Sensitivity Analysis System developed by Zaitsu et al. Details of the analysis conditions for each amino acid are explained in Miyoshi, Y. et al, J. Chromatogr. B, 879:3194 (2011) and Sasabe, J. et al, Proc. Natl. Acad. Sci. U.S.A., 109:627 (2012). Briefly speaking, amino acids present in serum and urine were derivatized with NBD-F (4-fluoro-7-nitro-2,1,3-benzoxadiazole, Tokyo Chemical Industry Co., Ltd.) and applied to an HPLC system (refer to supplementary information provided with Nanospace SI-2, Shiseido Japan Co., Ltd.). Briefly speaking, an in-house manufactured monolithic ODS column (internal diameter: 1.5 mm×250 mm, installed in quartz glass capillary tube) was used for the reversed-phase separation analytical column. Fluorescence was detected at an excitation wavelength of 470 nm and detection wavelength of 530 nm. The samples were transferred to an enantiomer selective column following reversed-phase separation. The Sumichiral OA-2500S column (250 mm×1.5 mm, packed in-house, material manufactured by Sumika Chemical Analysis Service, Ltd.) using (S)-naphthylglycine for the chiral center was used for enantiomer separation. Concentrations of D-amino acids in body fluids were maintained on the physiological micromole order. The two-dimensional HPLC system explained in the examples is able to quantitatively measure within a range of 1 fmol to 100 pmol by distinguishing stereoisomers of serine, for example. This sensitivity was sufficient for identifying changes in the concentrations of the D-form and L-form of serine in healthy individuals and renal failure patients (not shown in the drawings).

(6) Statistical Processing

All numerical values described in the present description and drawings are indicated as the standard error of the mean±sample mean (SEM). Statistical techniques such as the two-tailed Student's t-test, one-way analysis of variance (one way ANOVA) or Tukey's multiple comparison test were used for statistical analysis of experiment results. In addition, P values of less than 0.05 were evaluated as constituting a significant difference in these tests. Prism5 (GraphPad Software, La Hoya, Calif.) was used for all analyses.

2. Results (1) Serum D-Serine and L-Serine Concentrations

FIG. 1-A is a typical chromatogram obtained by two-dimensional HPLC of D-/L-serine in the serum of C57BL/6J wild-type mice that underwent sham surgery or ischemia reperfusion treatment. In the following experiment, markers were measured for 8 animals in a sham group and for 5, 9, 6 and 7 animals at 4, 8, 20 and 40 hours, respectively, after reperfusion. The bar graphs of FIGS. 1-A to 1-F represent average values, while the error bars represent the standard error of the sample mean (SEM). Data of the examples was tested statistically by one way analysis of variance followed by Tukey's multiple comparison test. In FIGS. 1-A to 1-F, one asterisk (*) indicates a P value of less than 0.05, two asterisks () indicate a P value of less than 0.01, and three asterisks (*) indicate a P value of less than 0.001. NS stands for not significant. The word "sham" in the drawings indicates concentrations in mice that underwent sham surgery, while IR14, IR18, IRI20 and IRI40 indicate concentrations in mice at 4, 8, 20 and 40 hours after reperfusion, respectively. Although there were significant fluctuations in serum D-serine concentrations at 4 and 8 hours after reperfusion in the C57BL/6J mice, concentrations increased at 20 hours and increased further at 40 hours (FIG. 1-B). Furthermore, the values of D-serine concentration indicated in FIG. 1-B were 3.7±0.4 µM in the sham surgery mice, 3.4±0.3 µM for IR14, 4.3±0.4 µM for IR18, 5.5±0.5 µM for IRI20 and 10.6±0.4 µM for IRI40. Serum L-serine concentrations decreased 4 hours after reperfusion and subsequently remained at a low value (FIG. 1-C). The values of L-serine concentration indicated in FIG. 1-C were 106.1±5.6 µM in the sham surgery mice, 46.9±0.6 µM for IR14, 61.5±5.6 µM for IR18, 70.6±7.5 µM for IRI20 and 64.7±2.2 µM for IRI40. Consequently, the ratio of [D-serine]/[L-serine] increased accompanying the decrease in L-serine concentration and increased further after 40 hours (FIG. 1-D). The values of [D-serine]/[L-serine] shown in FIG. 1-D were 0.036±0.004 in the sham surgery mice, 0.074±0.005 for IR14, 0.073±0.009 for IR18, 0.082±0.009 for IRI20 and 0.164±0.008 for IRI40. Serum creatinine concentrations increased starting 4 hours after reperfusion and increased further 40 hours after reperfusion (FIG. 1-E). The values of creatinine concentration indicated in FIG. 1-E were 0.59±0.05 mg/dl in the sham surgery mice, 1.108±0.04 mg/dl for IR14, 1.89±0.09 mg/dl for IR18, 1.14±0.22 mg/dl for IRI20 and 3.73±0.09 mg/dl for IRI40. However, serum cystatin C concentrations gradually decreased after 40 hours after having initially increased at 4 hours after reperfusion (FIG. 1-F). The values of cystatin C concentration indicated in FIG. 1-F were 0.84±0.01 µg/ml in the sham surgery mice, 1.63±0.08 µg/ml for IR14, 1.39±0.09 µg/ml for IR18, 1.19±0.05 µg/ml for IRI20 and 1.06±0.10 µg/ml for IRI40. On the basis of these experiments, the ratio of [D-serine]/[L-serine] began to increase 4 hours after reperfusion and then exhibited a monotonic increase until 40 hours after reperfusion, thereby clearly indicating that it is useful as a marker of renal failure. Here, although a certain value is only indicated at a certain point in time after reperfusion in the case of a monotonically changing marker, in the case of fluctuations having a peak and trough, a certain value is not only indicated at a single point in time, but may also increase another time or a plurality of times more. Consequently, the stage of progression of renal failure cannot be uniquely estimated by the value of a marker.

(2) Urine D-Serine and L-Serine

In the following experiment, markers were measured for 7 animals in a sham group and for 5 animals each at 4, 8, 20 and 40 hours after reperfusion. The bar graphs of FIGS. 2-A to 2-J represent average values, while the error bars represent the standard error of the sample mean (SEM). Data of the examples was tested statistically by one way analysis of variance followed by Tukey's multiple comparison test. In FIGS. 2-A to 2-G, one asterisk (*) indicates a P value of less than 0.05, two asterisks () indicate a P value of less than 0.01, and three asterisks (*) indicate a P value of less than 0.001. NS stands for not significant. Although serum D-serine concentrations increased with the passage of time after reperfusion, L-serine concentrations decreased. In urine, however, D-serine concentrations conversely decreased with the passage of time after reperfusion (FIG. 2-B), while L-serine concentrations increased (FIG. 2-C). The values of D-serine concentration indicated in FIG. 2-B were 52.0±7.6 µM in the sham surgery mice, 24.5±5.7 µM for IR14, 9.9±1.1 µM for IR18, 36.9±3.3 µM for IRI20 and 22.4±3.8

μM for IRI40. The values of L-serine indicated in FIG. 2-C were 19.0±3.0 μM in the sham surgery mice, 23.6±2.7 μM for IR14, 62.6±9.9 μM for IR18, 136.1±14.9 μM for IRI20 and 93.8±12.1 μM for IRI40. Furthermore, urine creatinine levels decreased starting 8 hours after reperfusion (FIG. 2-D). This is due to outflow of creatinine into the urine having been inhibited by depressed renal function. Although depression of renal function was not remarkable until 4 hours after reperfusion since creatinine levels did not differ that much from the sham surgery mice at 4 hours after reperfusion, the ratio of [D-serine]/[L-serine] in urine decreased to nearly one-third of that of the sham surgery mice after 4 hours (FIG. 2-E). Therefore, the ratio of [D-serine]/[L-serine] in urine fluctuated prior to depression of renal function, and since it decreased monotonically, it was indicated to be useful as an early marker of renal failure. The values of the ratio of [D-serine]/[L-serine] indicated in FIG. 2-E were 2.82±0.18 in the sham surgery mice, 1.10±0.26 for IR14, 0.16±0.01 for IR18, 0.28±0.02 for IRI20 and 0.25±0.04 for IRI40. Although urine KIM-1 concentrations increased through 20 hours after reperfusion, they decreased at 40 hours after reperfusion (FIG. 2-F). Urine NGAL concentrations did not differ significantly from the sham surgery mice at 4 hours after reperfusion, increased at 8 hours and subsequently remained substantially unchanged (FIG. 2-G). Thus, parameters based on urine serine concentration demonstrated fluctuations accompanying renal failure that started earlier than any of the known markers, and since those fluctuations changed monotonically, they are useful for determining the stage of the progression of renal failure of a subject.

(3) Changes in Concentration Ratios of Various Amino Acid Enantiomers in Urine

The concentrations of various amino acid enantiomer pairs were measured for the urine of two of the mice used in the experiment of FIG. 2-A to 2-J in which urine markers were measured. FIGS. 3-A to 3-L indicate bar graphs of the ratio of the average value of the concentration of a D-form to the average value of the concentration of an L-form of individual mice for the mice at 4, 8, 20 and 40 hours after ischemia reperfusion treatment. As a result, in the case of [D-glutamic acid] and [L-glutamic acid] (FIG. 3-F), [D-allo-isoleucine] and [L-isoleucine] (FIG. 3-J) and [D-phenylalanine] and [L-phenylalanine] (FIG. 3-K) in urine, the ratio of the concentration of the D-form to the concentration of the L-form did not fluctuate 4 hours after reperfusion, decreased considerably starting 8 hours after reperfusion. In contrast, in the combinations of [D-histidine] and [L-histidine] (FIG. 3-A), [D-asparagine] and [L-asparagine] (FIG. 3-B), [D-serine] and [L-serine] (FIG. 3-C), [D-arginine] and [L-arginine] (FIG. 3-D), [D-allo-threonine] and [L-threonine] (FIG. 3-E), [D-alanine] and [L-alanine] (FIG. 3-G), [D-proline] and [L-proline] (FIG. 3-H), [D-valine] and [L-valine] (FIG. 3-I) and [D-lysine] and [L-lysine] (FIG. 3-L), the ratio of the concentration of the D-form to the concentration of the L-form fluctuated considerably at 4 hours after reperfusion, demonstrating values intermediate to the sham surgery mice and values starting 8 hours after reperfusion. Therefore, if at least one of any of [D-histidine]/[L-histidine], [D-asparagine]/[L-asparagine], [D-arginine]/[L-arginine], [D-allo-threonine]/[L-threonine], [D-alanine]/[L-alanine], [D-proline]/[L-proline], [D-valine]/[L-valine] and [D-lysine]/[L-lysine] in a certain individual is lower than the value of a healthy individual, even if at least any one of [D-glutamic acid]/[L-glutamic acid], [D-allo-i-allo-isoleucine]/[L-isoleucine] and [D-phenylalanine]/[L-phenylalanine] has a value that is no different from the value of a healthy individual, an extremely early state prior to the onset of depression of renal function can be detected. In addition, when at least one of any of [D-histidine]/[L-histidine], [D-asparagine]/[L-asparagine], [D-arginine]/[L-arginine], [D-allo-threonine]/[L-threonine], [D-alanine]/[L-alanine], [D-proline]/[L-proline], [D-valine]/[L-valine] and [D-lysine]/[L-lysine] in a certain individual is lower than the value of a healthy individual, and at least any one of [D-glutamic acid]/[L-glutamic acid], [D-allo-isoleucine]/[L-isoleucine] and [D-phenylalanine]/[L-phenylalanine] is lower than the value of a healthy individual, a state at a time when depression of renal function has begun is detected. In this manner, not only whether or not a subject is in the early stage of renal failure, but also an extremely early stage prior to the onset of depression of renal function, or even a state at the time depression of renal function has begun, can be distinguished by parameters based on the urine concentrations of the D-forms and L-forms of different groups of amino acids.

(4) Changes in Percentage of Concentration of D-Form to the Total

Concentrations of Various Amino Acid Enantiomers in Urine

FIGS. 4-A to 4-L indicate bar graphs of the percentages of the average values of concentrations of a D-form to the sum of the average values of the concentrations of an L-form and the average values of the concentrations of the D-form of individual mice for sham surgery mice and mice 4, 8, 20 and 40 hours after ischemia reperfusion treatment. As a result, in the case of [D-glutamic acid] and [L-glutamic acid] (FIG. 4-F), [D-allo-isoleucine] and [L-isoleucine] (FIG. 4-J) and [D-phenylalanine] and [L-phenylalanine] (FIG. 4-K) in urine, the percentage of the average value of the concentration of the D-form to the sum of the average value of the concentration of the L-form and the average value of the concentration of D-form did not fluctuate even at 4 hours after reperfusion, and decreased considerably starting 8 hours after reperfusion. In contrast, in the combinations of [D-histidine] and [L-histidine] (FIG. 4-A), [D-asparagine] and [L-asparagine] (FIG. 4-B), [D-serine] and [L-serine] (FIG. 4-C), [D-arginine] and [L-arginine] (FIG. 4-D), [D-allo-threonine] and [L-threonine] (FIG. 4-E), [D-alanine] and [L-alanine] (FIG. 4-G), [D-proline] and [L-proline] (FIG. 4-H), [D-valine] and [L-valine] (FIG. 4-I) and [D-lysine] and [L-lysine] (FIG. 4-L), the percentage of the average value of the concentration of the D-form to the sum of the average value of the concentration of the L-form and the average value of the concentration of the D-form fluctuated considerably 4 hours after reperfusion, demonstrating values intermediate to the sham surgery mice and values starting 8 hours after reperfusion. Therefore, if at least one of any of the percentage of [D-histidine] to [total histidine], the percentage of [D-asparagine] to [total asparagine], the percentage of [D-arginine] to [total arginine], the percentage of [D-allo-threonine] to the sum of [D-allo-threonine] and [L-threonine], the percentage of [D-alanine] to [total alanine], the percentage of [D-proline] to [total proline], the percentage of [D-valine] to [total valine], and the percentage of [D-lysine] to [total lysine] in a certain individual is lower than the value of a healthy individual, even if at least any one of the percentage of [D-glutamic acid] to [total glutamic acid], the percentage of [D-allo-isoleucine] to the sum of [D-allo-isoleucine] and [L-isoleucine] and the percentage of [D-phenylalanine] to [total phenylalanine] is no different from the value of a healthy individual, an extremely early state prior to the onset of depression of renal function can be detected.

In addition, when at least one of any of the percentage of [D-histidine] to [total histidine], the percentage of [D-asparagine] to [total asparagine], the percentage of [D-arginine] to [total arginine], the percentage of [D-allo-threonine] to the sum of [D-allo-threonine] and [L-threonine], the percentage of [D-alanine] to [total alanine], the percentage of [D-proline] to [total proline], the percentage of [D-valine] to [total valine], and the percentage of [D-lysine] to [total lysine] in a certain individual is lower than the value of a healthy individual, and at least one of any of the percentages of [D-glutamic acid] to [total glutamic acid], the percentage of [D-allo-isoleucine] to the sum of [D-allo-isoleucine] and [L-isoleucine] and the percentage of [D-phenylalanine] to [total phenylalanine] is also lower than the value of a healthy individual, a state at a time when depression of renal function has begun is detected. In this manner, not only whether or not a subject is in the early stage of renal failure, but also an extremely early stage prior to the onset of depression of renal function, or even a state at the time depression of renal function has begun, can be distinguished by parameters based on the urine concentrations of the D-forms and L-forms of different groups of amino acids.

(5) Changes in Concentration Ratios of Various Amino Acid Enantiomers in Urine

Ischemia reperfusion treatment was performed on 3 to 7 mice and the concentrations of various amino acid enantiomer pairs were measured in the acquired urine. FIGS. 5-A to 5-R indicate bar graphs of the ratios of the average value of the concentration of a D-form to the average value of the concentration of an L-form in individual mice in sham-surgery mice and mice at 4, 8, 20 and 40 hours after ischemia reperfusion treatment along with the results of investigating for the presence or absence of statistically significant differences. As a result, in the case of [D-allo-isoleucine] and [L-isoleucine] (FIG. 5-J), [D-phenylalanine] and [L-phenylalanine] (FIG. 5-K) and [D-leucine] and [L-leucine] (FIG. 5-R) in urine, the ratio of the concentration of the D-form to the concentration of the L-form did not fluctuate even at 4 hours after reperfusion (absence of significant difference) and decreased considerably starting 8 hours after reperfusion (presence of significant difference). In the case of [D-glutamic acid] and [L-glutamic acid] (FIG. 5-F), [D-valine] and [L-valine] (FIG. 5-I), [D-glutamine] and [L-glutamine] (FIG. 5-M), [D-threonine] and [L-threonine] (FIG. 5-N) and [D-allo-threonine] and [L-allo-threonine] (FIG. 5-Q), although values fluctuated even at 4 hours after reperfusion, there were no statistically significant differences, while values decreased considerably starting at 8 hours after reperfusion (presence of significant difference). In the case of [D-methionine] and [L-methionine] (FIG. 5-O) and [D-aspartic acid] and [L-aspartic acid] (FIG. 5-P), there were no fluctuating tendencies observed. In contrast, in the combinations of [D-histidine] and [L-histidine] (FIG. 5-A), [D-asparagine] and [L-asparagine] (FIG. 5-B), [D-serine] and [L-serine] (FIG. 5-C), [D-arginine] and [L-arginine] (FIG. 5-D), [D-allo-threonine] and [L-threonine] (FIG. 5-E), [D-alanine] and [L-alanine] (FIG. 5-G), [D-proline] and [L-proline] (FIG. 5-H) and [D-lysine] and [L-lysine] (FIG. 5-L), the ratio of the concentration of the D-form to the concentration of the L-form fluctuated considerably at 4 hours after perfusion (presence of statistically significant difference), demonstrating values intermediate to the sham surgery mice and values starting at 8 hours after reperfusion. In the case of urine creatinine conventionally used as a diagnostic marker of renal failure, since renal failure was unable to be detected at 4 hours after reperfusion and was only able to be detected starting at 8 hours after reperfusion in a ischemia reperfusion model using mice (FIG. 2-D), any of the [D-allo-isoleucine] and [L-isoleucine], [D-phenylalanine] and [L-phenylalanine], [D-leucine] and [L-leucine], [D-glutamic acid] and [L-glutamic acid], [D-valine] and [L-valine], [D-glutamine] and [L-glutamine], [D-threonine] and [L-threonine], [D-allo-threonine] and [L-allo-threonine], [D-histidine] and [L-histidine], [D-asparagine] and [L-asparagine], [D-serine] and [L-serine], [D-arginine] and [L-arginine], [D-allo-threonine] and [L-threonine], [D-alanine] and [L-alanine], [D-proline] and [L-proline] (FIG. 5-H) and [D-lysine] and [L-lysine] (FIG. 5-L) can be used as a marker for renal failure having sensitivity that is equal to or greater than that of urine creatinine. If one or a plurality of pathological index values selected from the group consisting of [D-histidine]/[L-histidine], [D-asparagine]/[L-asparagine], [D-arginine]/[L-arginine], [D-allo-threonine]/[L-threonine], [D-alanine]/[L-alanine], [D-proline]/[L-proline] and [D-lysine]/[L-lysine], which are capable of detection at 4 hours after reperfusion with a significant difference in particular, is used, renal failure can be diagnosed with higher sensitivity than urine creatinine. Among these, one or a plurality of pathology index values selected from the group consisting of [D-histidine]/[L-histidine], [D-asparagine]/[L-asparagine], [D-proline]/[L-proline] and [D-lysine]/[L-lysine], which demonstrate a significant difference of P<0.01 with the sham surgery group at 4 hours after reperfusion, in particular is capable of diagnosing renal failure with higher sensitivity, while one or a plurality of pathological index values selected from the group consisting of [D-histidine]/[L-histidine], [D-proline]/[L-proline] and [D-lysine]/[L-lysine], which demonstrate a significant difference of P<0.001 with the sham surgery group at 4 hours after reperfusion, is capable of diagnosing renal failure with even higher sensitivity. Although pathological index values may be used alone, combining a plurality of pathological index values enables diagnoses having a higher level of reliability.

In addition, among the pathological index values of the present invention, pathological index values calculated using the concentrations of any of the pairs of D-forms and L-forms among [D-allo-isoleucine] and [L-isoleucine], [D-phenylalanine] and [L-phenylalanine], [D-leucine] and [L-leucine], [D-glutamic acid] and [L-glutamic acid], [D-valine] and [L-valine], [D-glutamine] and [L-glutamine], [D-threonine] and [L-threonine], [D-alto-threonine] and [L-allo-threonine], [D-histidine] and [L-histidine], [D-asparagine] and [L-asparagine], [D-serine] and [L-serine], [D-arginine] and [L-arginine], [D-allo-threonine] and [L-threonine], [D-alanine] and [L-alanine], [D-proline] and [L-proline] (FIG. 5-H) and [D-lysine] and [L-lysine] can be used as markers of renal failure having sensitivity that is equal to or greater than that of urine creatinine. Thus, in the case a pathological index value of a subject is statistically significantly different from the pathological index reference value of a healthy individual group and statistically significantly different from the pathological index reference value of a renal failure patient group, and is between the pathological index reference value of a healthy individual group and the pathological index reference value of a renal failure patient group, the subject can be diagnosed as being suspected of early renal failure. In particular, the use of a pathological index value calculated using the concentration of one or a plurality of a pair of D-form and L-form of one or more amino acids selected from the group consisting of [D-histidine] and [L-histidine], [D-asparagine] and [L-asparagine], [D-proline] and [L-proline] and [D-lysine] and [L-lysine], which exhibit a significant difference of p<0.01 with a sham surgery group at 4 hours after reperfusion, enables diagnosis of renal failure at an earlier stage. Moreover, renal failure can be diagnosed at an even earlier stage by using a pathological index value calculated from the concentration of one or a plurality of a pair of D-form and L-form of one or more amino acids selected from the group consisting of [D-histidine] and [L-histidine], [D-proline] and [L-proline] and [D-lysine] and [L-lysine], which exhibit a significant difference of $p<0.001$ with a sham surgery group at 4 hours after reperfusion.

The invention claimed is:

1. A method of diagnosing and treating a renal failure comprising obtaining a urine sample from a subject;
measuring concentrations of D-serine and L-serine in the urine sample of the subject;
calculating a value of a pathological index for the subject based on the measured concentrations of D-serine and L-serine in the urine sample of the subject;
determining that the subject has the renal failure or is suspected of having an early stage of the renal failure if the calculated value of the pathological index for the subject is statistically different compared to a healthy individual group pathological index reference value; and
treating the renal failure in the subject who is determined to have the renal failure or is suspected of having an early stage of the renal failure, wherein the treating comprises administering to the subject a renal failure therapeutic drug that inhibits the progression or improves the renal failure and the drug is at least one selected from the group comprising antihypertensive drugs, antidiabetic drugs, antidyslipidemic drugs, antianemic drugs, therapeutic drugs for bone and mineral metabolic disorders, therapeutic drugs for hyperuricemia, therapeutic drugs for uremic toxins, therapeutic drugs for hyperkalemia and therapeutic drugs for hyperphosphatemia.

2. The method of claim 1, the treating comprises inhibiting the progression or improving the renal failure.

3. The method of claim 1, wherein the drug is at least one selected from the group comprising antihypertensive drugs, antidiabetic drugs, antidyslipidemic drugs, antianemic drugs, therapeutic drugs for bone and mineral metabolic disorders, therapeutic drugs for hyperuricemia, and therapeutic drugs for uremic toxins.

4. The method of claim 3, wherein the drug is at least one selected from the group comprising angiotensin-converting enzymes, angiotensin II receptor antagonists, α-glucosidase inhibitors, insulin preparations, HMG-CoA reductase inhibitors, intestinal cholesterol transporter inhibitors, recombinant human erythropoietin preparations and spherical adsorbent carbon medications.

5. The method of claim 1, wherein the drug is selected from a therapeutic drug for hyperkalemia and a therapeutic drug for hyperphosphatemia.

6. The method of claim 1, wherein said determining comprises
a) determining that the subject does not have the renal failure if the calculated value of the pathological index for the subject is statistically similar to a healthy individual group pathological index reference value;
b) determining that the subject has the renal failure if the calculated value of the pathological index for the subject is statistically similar to an acute or chronic renal failure patient pathological index reference value; and
c) determining that the subject is suspected of having an early stage of the renal failure if the calculated value of the pathological index for the subject is between a healthy individual group pathological index reference value and an acute or chronic renal failure patient pathological index reference value.

7. The method of claim 6, wherein when the subject is determined to be suspected of having an early stage of the renal failure, the renal failure is improved or the progression of the renal failure is inhibited, before the subject exhibits blood creatinine level fluctuations.

8. The method of claim 7, wherein the drug is selected from the group comprising antihypertensive drugs, antidiabetic drugs, antidyslipidemic drugs, antianemic drugs, therapeutic drugs for bone and mineral metabolic disorders, therapeutic drugs for hyperuricemia, and therapeutic drugs for uremic toxins.

9. The method of claim 8, wherein the drug is at least one selected from the group comprising angiotensin-converting enzymes, angiotensin II receptor antagonists, α-glucosidase inhibitors, insulin preparations, HMG-CoA reductase inhibitors, intestinal cholesterol transporter inhibitors, recombinant human erythropoietin preparations and spherical adsorbent carbon medications.

10. The method of claim 7, wherein the drug is selected from a therapeutic drug for hyperkalemia and a therapeutic drug for hyperphosphatemia.

11. The method of claim 1, which does not comprise measuring a volume of the urine sample and wherein said calculating does not comprise correcting for the volume of the urine sample.

12. The method of claim 11, wherein said calculating comprises calculating a ratio between the measured concentration of D-serine and the measured concentration of L-serine or calculating a ratio between the measured concentration of D-serine and a sum of the measured concentration of D-serine and the measured concentration of L-serine.

13. The method of claim 1, further comprising measuring a pair of concentrations of D-form and L-form of amino acids other than serine, using a pathological index calculated from the pair of concentrations in combination with said pathological index to determine that the subject has the renal failure or is suspected of having an early stage of the renal failure.

14. The method of claim 1, wherein said measuring is performed by a separation analysis system comprising an enantiomer selective column.

15. The method of claim 13, wherein said measuring steps are performed by a separation analysis system comprising an enantiomer selective column.

16. The method of claim 14, wherein the separation analysis system is a HPLC system.

17. The method of claim 15, wherein the separation analysis system is a HPLC system.

* * * * *